(12) United States Patent
Birch et al.

(10) Patent No.: US 7,749,997 B2
(45) Date of Patent: Jul. 6, 2010

(54) PYRIMIDO [4,5-B] -OXAZINES FOR USE AS DGAT INHIBITORS

(75) Inventors: Alan Martin Birch, Macclesfield (GB); Paul David Kemmitt, Macclesfield (GB)

(73) Assignee: AstraZeneca AB, Sodertalje (CH)

( * ) Notice: Subject to any disclaimer, the term of this patent is extended or adjusted under 35 U.S.C. 154(b) by 0 days.

(21) Appl. No.: 12/158,252

(22) PCT Filed: Dec. 19, 2006

(86) PCT No.: PCT/GB2006/004761

§ 371 (c)(1),
(2), (4) Date: Jun. 19, 2008

(87) PCT Pub. No.: WO2007/071966

PCT Pub. Date: Jun. 28, 2007

(65) Prior Publication Data

US 2008/0306059 A1    Dec. 11, 2008

Related U.S. Application Data

(60) Provisional application No. 60/753,312, filed on Dec. 22, 2005.

(51) Int. Cl.
C07D 498/04 (2006.01)
A61K 31/5365 (2006.01)

(52) U.S. Cl. .................. 514/230.5; 544/105

(58) Field of Classification Search ........... 544/105; 514/230.5
See application file for complete search history.

(56) References Cited

U.S. PATENT DOCUMENTS

| | | | |
|---|---|---|---|
| 4,983,731 A | 1/1991 | Wagner et al. | |
| 5,491,172 A | 2/1996 | Lee et al. | |
| 6,608,185 B1 | 8/2003 | Omura et al. | |
| 6,624,185 B2 | 9/2003 | Glombik et al. | |
| 7,138,414 B2 | 11/2006 | Schoenafinger et al. | |
| 7,453,010 B2 | 11/2008 | Bovy et al. | |
| 2002/0183384 A1 | 12/2002 | Cornicelli et al. | |
| 2003/0072757 A1 | 4/2003 | Farese et al. | |
| 2004/0102432 A1 | 5/2004 | Sanganee et al. | |
| 2005/0070545 A1 | 3/2005 | Fox et al. | |
| 2007/0123504 A1 | 5/2007 | Bolin et al. | |
| 2007/0155832 A1 | 7/2007 | Haeberlein et al. | |
| 2007/0249620 A1 | 10/2007 | Kurata et al. | |
| 2008/0090876 A1 | 4/2008 | Cheng et al. | |
| 2008/0096874 A1 | 4/2008 | Birch et al. | |
| 2009/0048258 A1 | 2/2009 | Ogino et al. | |
| 2009/0093497 A1 | 4/2009 | Bolin et al. | |
| 2009/0197926 A1 | 8/2009 | Birch et al. | |
| 2009/0209602 A1 | 8/2009 | Butlin et al. | |
| 2009/0215779 A1 | 8/2009 | Butlin et al. | |
| 2009/0275620 A1 | 11/2009 | Butlin et al. | |
| 2009/0298853 A1 | 12/2009 | Bauer et al. | |

FOREIGN PATENT DOCUMENTS

| | | |
|---|---|---|
| DE | 10223273 | 12/2003 |
| EP | 1236468 | 9/2002 |
| JP | 2004/067635 | 3/2004 |
| JP | 2005/206492 | 8/2005 |
| JP | 2007/131584 | 5/2007 |
| JP | 2007/191471 | 8/2007 |
| WO | WO 94/26702 | 11/1994 |
| WO | WO 00/58491 | 10/2000 |
| WO | WO 02/20484 | 3/2002 |
| WO | WO 03/099772 | 12/2003 |
| WO | WO 2004/007455 | 1/2004 |
| WO | WO 2004/047755 | 6/2004 |
| WO | WO 2004047755 A2 * | 6/2004 |
| WO | WO 2004/100881 | 11/2004 |
| WO | WO 2005/013907 | 2/2005 |
| WO | WO 2005/044250 | 5/2005 |
| WO | WO 2005/046670 | 5/2005 |
| WO | WO 2005/072740 | 8/2005 |
| WO | WO 2006/004200 | 1/2006 |
| WO | WO 2006/019020 | 2/2006 |
| WO | WO 2006/044775 | 4/2006 |
| WO | WO 2006/064189 | 6/2006 |
| WO | WO 2006/082010 | 8/2006 |
| WO | WO 2006/082952 | 8/2006 |
| WO | WO 2006/113919 | 10/2006 |
| WO | WO 2006/120125 | 11/2006 |

(Continued)

OTHER PUBLICATIONS

Adcock and Cox "Electronic nature of the tricyanomethyl group by 13C and 19F NMR: Nature of aryl 19F NMR polar field effects in the benzene and naphthalene ring systems" Journal of Organic Chemistry, 44(17):3004-3017 (1979).

(Continued)

*Primary Examiner*—Kahsay T Habte
(74) *Attorney, Agent, or Firm*—Morgan Lewis & Bockius LLP

(57) ABSTRACT

Compounds of formula (I) or salts thereof, wherein A, and $R^1$ to $R^5$ are as defined in the specification, are DGAT-1 inhibitors and are thereby useful in the treatment of, for example, obesity. Processes to make compounds of formula (I) are also described.

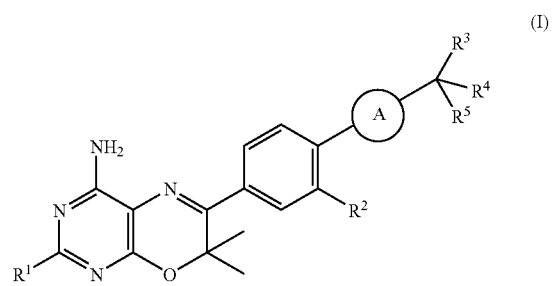

4 Claims, 1 Drawing Sheet

FOREIGN PATENT DOCUMENTS

| | | |
|---|---|---|
| WO | WO 2006/134317 | 12/2006 |
| WO | WO 2007/016538 | 2/2007 |
| WO | WO 2007/060140 | 5/2007 |
| WO | WO 2007/126957 | 11/2007 |
| WO | WO 2007/137103 | 11/2007 |
| WO | WO 2007/137107 | 11/2007 |
| WO | WO 2007/138304 | 12/2007 |
| WO | WO 2007/138311 | 12/2007 |
| WO | WO 2007/141502 | 12/2007 |
| WO | WO 2007/141517 | 12/2007 |
| WO | WO 2007/141538 | 12/2007 |
| WO | WO 2007/141545 | 12/2007 |
| WO | WO 2007/144571 | 12/2007 |
| WO | WO 2008/011130 | 1/2008 |
| WO | WO 2008/011131 | 1/2008 |
| WO | WO 2008/039007 | 4/2008 |
| WO | WO 2008/039008 | 4/2008 |
| WO | WO 2008/040651 | 4/2008 |
| WO | WO 2008/048991 | 4/2008 |
| WO | WO 2008/067257 | 6/2008 |
| WO | WO 2008/099221 | 8/2008 |
| WO | WO 2008/129319 | 10/2008 |
| WO | WO 2008/134690 | 11/2008 |
| WO | WO 2008/134693 | 11/2008 |
| WO | WO 2008/141976 | 11/2008 |
| WO | WO 2008/148840 | 12/2008 |
| WO | WO 2008/148849 | 12/2008 |
| WO | WO 2008/148851 | 12/2008 |
| WO | WO 2008/148868 | 12/2008 |
| WO | WO 2009/011285 | 1/2009 |
| WO | WO 2009/016462 | 2/2009 |
| WO | WO 2009/024821 | 2/2009 |
| WO | WO 2009/037222 | 3/2009 |
| WO | WO 2009/040410 | 4/2009 |
| WO | WO 2009/071483 | 6/2009 |
| WO | WO 2009/081195 | 7/2009 |
| WO | WO 2009/112445 | 9/2009 |

OTHER PUBLICATIONS

Anderson et al. "Identification of a Form of Acyl-CoA:Cholesterol Acyltransferase Specific to Liver and Intestine in Nonhuman Primates" J Biol Chem 273(41):26747-26754 (1998).

Birch et al. "Discovery of a Potent, Selective, and Orally Efficacious Pyrimidinooxazinyl Bicyclooctaneacetic Acid Diacylglycerol Acyltransferase-1 Inhibitor" J. Med. Chem. 52(6):1558-1568 (2009).

Brown and Goldstein "Lipoprotein metabolism in the macrophage: implications for cholesterol deposition in atherosclerosis" Annu Rev Biochem. 52:223-261 (1983).

Burnett and Huff "Avasimibe Pfizer" Curr Opin Investig Drugs 3(9):1328-1333 (2002).

CAPLUS RN 404032-15-1, retrieved from CAPLUS on Jul. 17, 2009.

Cases et al. "ACAT-2, A Second Mammalian Acyl-CoA:Cholesterol Acyltransferase" J Biol Chem 273(41):26755-26764 (1998).

Cases et al. "Cloning of DGAT2, a Second Mammalian Diacylglycerol Acyltransferase, and Related Family Members" J. Biol. Chem. 276(42):38870-38876 (2001).

Cases et al. "Identification of a gene encoding an acyl CoA:diacylglycerol acyltransferase, a key enzyme in triacylglycerol synthesis" Proc Natl Acad Sci U S A. 95(22):13018-13023 (1998).

Chang et al. "Molecular cloning and functional expression of human acyl-coenzyme A:cholesterol acyltransferase cDNA in mutant Chinese hamster ovary cells" J. Biol. Chem. 268(28):20747-20755 (1993).

Chen et al. "Increased Insulin and Leptin Sensitivity in Mice Lacking ACYL COA: Diacylglycerol Acyltransferase 1" Journal of Clinical Investigation 109(8):1049-1055 (2002).

Chen et al. "Inhibition of Triglyceride Synthesis as a Treatment Strategy for Obesity: Lessons From DGAT1-Deficient Mice" Arteriosclerosis, Thrombosis, and Vascular Biology 25(3): 482-486 (2005).

Chen et al. "Obesity resistance and enhanced glucose metabolismin mice transplanted with white adipose tissue lacking acyl CoA:diacylglycerol acyltransferase 1" J. Clin. Invest. 111(11):1715-1722 (2003).

Coleman "Diacylglycerol acyltransferase and monoacylglycerol acyltransferase from liver and intestine" Methods in Enzymology 209:98-104 (1992).

Field and Salome "Effect of dietary fat saturation, cholesterol and cholestyramine on acyl-CoA: cholesterol acyltransferase activity in rabbit intestinal microsomes" Biochimica et Biophysica Acta 712(3):557-570 (1982).

Hoffman et al. "Synthesis and evaluation of 2-pyridinone derivatives as HIV-1-specific reverse transcriptase inhibitors. 4. 3-[2-(Benzoxazol-2-yl)ethyl]-5-ethyl-6-methylpyridin-2(1H)-one and analogs" Journal of Medicinal Chemistry 36(8):953-966 (1993).

Hubbard et al. "Antisense and small-molecule modulation of diacylglycerol acyltransferase" Expert Opinion on Therapeutic Patents 17(11): 1331-1339 (2007).

Insull Jr. et al. "Efficacy and short-term safety of a new ACAT inhibitor, avasimibe, on lipids, lipoproteins, and apolipoproteins, in patients with combined hyperlipidemia" Atherosclerosis 157(1):137-144 (2001).

Lehner and Kuksis "Biosynthesis of triacylglycerols" Prog Lipid Res. 35(2):169-201 (1996).

Oelkers et al. "Characterization of Two Human Genes Encoding Acyl Coenzyme A:Cholesterol Acyltransferase—related Enzymes" J Biol Chem 273(41):26765-26771 (1998).

Robertson et al. "Preclinical Safety Evaluation of Avasimibe in Beagle Dogs: An ACAT Inhibitor with Minimal Adrenal Effects" Toxicological Sciences 2001 US, 59(2):324-334 (2001).

Sawhney et al. "Synthesis of some 2-(5-substituted 1,3,4-oxadiazol-2-yl)-, 2-(5-substituted 1,3,4-thiadiazol-2-yl)- and 2-(3-mercapto-4-substituted-4H-1,2,4-triazol-5 -yl)- benzimidazoles as potential antiinflammatory agents" Indian Journal of Chemistry Section B, 30B:407-412 (1991).

Smith et al. "Obesity resistance and multiple mechanisms of triglyceride synthesis in mice lacking Dgat" Nature Genetics 25:87-90 (2000).

Yen et al. "Identification of a gene encoding MGAT1, a monoacylglycerol acyltransferase" Proc Natl Acad Sci U S A. 99(13):8512-8517 (2002).

Yen et al. "Thematic Review Series: Glycerolipids. DGAT enzymes and triacylglycerol biosynthesis" Journal of Lipid Research 49: 2283-2301 (2008).

Zammit et al. "Diacylglycerol acyltransferases: Potential roles as pharmacological targets" Pharmacology & Therapeutics 118(3):295-302 (2008).

Zhao et al. "Validation of diacyl glycerolacyltransferase I as a novel target for the treatment of obesity and dyslipidemia using a potent and selective small molecule inhibitor" J. Med. Chem. 51:380-383 (2008).

* cited by examiner

Figure 1: X-Ray Powder Diffraction Pattern for crystalline Example 1 (non-hydrate)
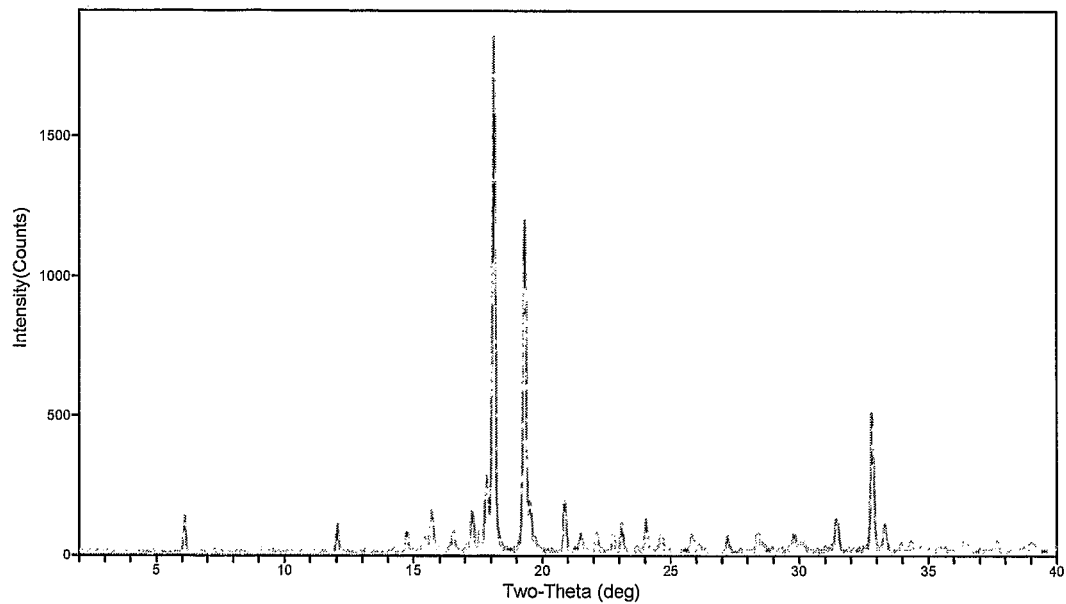
Figure 2: X-Ray Powder Diffraction Pattern for Example 1 as acetic acid solvate
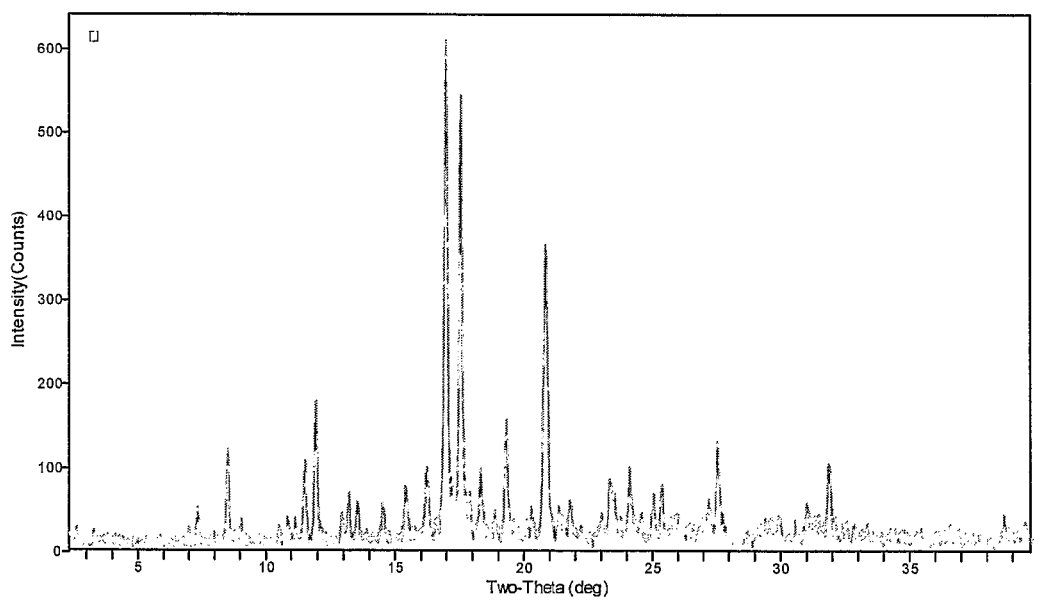

PYRIMIDO [4,5-B] -OXAZINES FOR USE AS DGAT INHIBITORS

RELATED APPLICATIONS

The present application is a U.S. National Phase Application of International Application No. PCT/GB2006/004761 (filed Dec. 19, 2006) which claims the benefit of U.S. Provisional Application No. 60/753,312 (filed Dec. 22, 2005), both of which are hereby incorporated by reference in their entirety.

The present invention relates to compounds which inhibit acetyl CoA (acetyl coenzyme A):diacylglycerol acyltransferase (DGAT1) activity, processes for their preparation, pharmaceutical compositions containing them as the active ingredient, methods for the treatment of disease states associated with DGAT1 activity, to their use as medicaments and to their use in the manufacture of medicaments for use in the inhibition of DGAT1 in warm-blooded animals such as humans. In particular this invention relates to compounds useful for the treatment of type II diabetes, insulin resistance, impaired glucose tolerance and obesity in warm-blooded animals such as humans, more particularly to the use of these compounds in the manufacture of medicaments for use in the treatment of type II diabetes, insulin resistance, impaired glucose tolerance and obesity in warm-blooded animals such as humans.

Acyl CoA:diacylglycerol acyltransferase (DGAT) is found in the microsomal fraction of cells. It catalyzes the final reaction in the glycerol phosphate pathway, considered to be the main pathway of triglyceride synthesis in cells by facilitating the acylation of a diacylglycerol with a fatty acyl CoA, resulting in the formation of triglyceride. Although it is unclear whether DGAT is rate-limiting for triglyceride synthesis, it catalyzes the only step in the pathway that is committed to producing this type of molecule [Lehner & Kuksis (1996) "Biosynthesis of triacylglycerols" Prog. Lipid Res. 35: 169-201].

Two DGAT genes have been cloned and characterised. Both of the encoded proteins catalyse the same reaction although they share no sequence homology. The DGAT1 gene was identified from sequence database searches because of its similarity to acyl CoA:cholesterol acyltransferase (ACAT) genes. [Cases et al (1998) "Identification of a gene encoding an acyl CoA:diacylglycerol acyltransferase, a key enzyme in triacylglycerol synthesis" Proc. Natl. Acad. Sci. USA 95: 13018-13023]. DGAT1 activity has been found in many mammalian tissues, including adipocytes.

Because of the previous lack of molecular probes, little is known about the regulation of DGAT1. DGAT1 is known to be significantly up-regulated during adipocyte differentiation.

Studies in gene knockout mice has indicated that modulators of the activity of DGAT1 would be of value in the treatment of type II diabetes and obesity. DGAT1 knockout (Dgat1$^{-/-}$) mice are viable and capable of synthesizing triglycerides, as evidenced by normal fasting serum triglyceride levels and normal adipose tissue composition. Dgat1$^{-/-}$ mice have less adipose tissue than wild-type mice at baseline and are resistant to diet-induced obesity. Metabolic rate is ~20% higher in Dgat1$^{-/-}$ mice than in wild-type mice on both regular and high-fat diets [Smith et al (2000) "Obesity resistance and multiple mechanisms of triglyceride synthesis in mice lacking DGAT" Nature Genetics 25: 87-90]. Increased physical activity in Dgat1$^{-/-}$ mice partially accounts for their increased energy expenditure. The Dgat1$^{-/-}$ mice also exhibit increased insulin sensitivity and a 20% increase in glucose disposal rate. Leptin levels are 50% decreased in the Dgat1$^{-/-}$ mice in line with the 50% decrease in fat mass.

When Dgat1$^{-/-}$ mice are crossed with ob/ob mice, these mice exhibit the ob/ob phenotype [Chen et al (2002) "Increased insulin and leptin sensitivity in mice lacking acyl CoA:diacylglycerol acyltransferase" J. Clin. Invest. 109: 1049-1055] indicating that the Dgat1$^{-/-}$ phenotype requires an intact leptin pathway. When Dgat1$^{-/-}$ mice are crossed with Agouti mice a decrease in body weight is seen with normal glucose levels and 70% reduced insulin levels compared to wild type, agouti or ob/ob/ Dgat1$^{-/-}$ mice.

Transplantation of adipose tissue from Dgat1$^{-/-}$ mice to wild type mice confers resistance to diet-induced obesity and improved glucose metabolism in these mice [Chen et al (2003) "Obesity resistance and enhanced glucose metabolism in mice transplanted with white adipose tissue lacking acyl CoA:diacylglycerol acyltransferase" J. Clin. Invest. 111: 1715-1722].

Therefore there is an ongoing need to find new DGAT inhibitors.

International Patent Application WO2004/047755 (Tularik and Japan Tabacco) describes fused bicyclic nitrogen-containing heterocycles which are inhibitors of DGAT-1. Many of the compounds in WO2004/047755 contain sidechains which include a disubstituted monocycloalkane, especially cyclohexane. We have surprisingly found that corresponding bicycloalkane and tricycloalkane containing compounds are also potent inhibitors of DGAT, and may have improved pharmacokinetic properties, particularly lower metabolic clearance and longer half-life. These improved properties would be expected to result advantageously in a low and/or once-daily therapeutic dose in human patients with a potential concomitant advantage in terms of side-effect profile and/or patient compliance and/or lowered cost of goods.

Accordingly, the present invention provides a compound of formula (I)

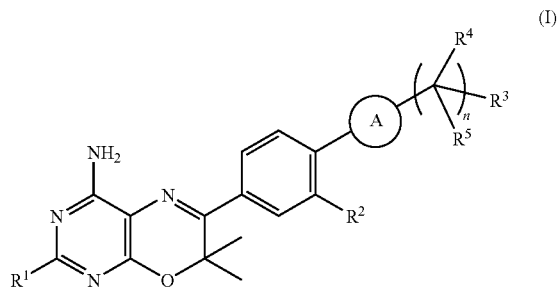

or a salt thereof, wherein:
R$^1$ is selected from hydrogen, methyl and trifluoromethyl;
R$^2$ is hydrogen, chloro or fluoro;
Ring A is (7-10C)bicycloalkanediyl or (8-12C)tricycloalkanediyl;
R$^3$ is carboxy or a carboxylic acid mimic or bioisostere;
R$^4$ and R$^5$ are each independently hydrogen or methyl;
n is 0 or 1.

In another aspect of the invention, there is provided a compound of formula (I) as defined above, or a salt thereof, wherein n is 1 and Ring A is (7-10C)bicycloalkanediyl.

In this specification the term (7-10C)bicycloalkanediyl includes bicyclo[2.2.1]heptanediyl, 1,4-bicyclo[2.2.2]octanediyl, 1,5-bicyclo[3.2.1]octanediyl, 1,5-bicyclo[3.2.2]nonanediyl, 1,5-bicyclo[3.3.2]decanediyl.

In this specification the term (8-12C)tricycloalkanediyl includes adamantyl.

It will be understood that when n=0 then the $R^3$ group is directly attached to Ring A. When n=1 then the group —C($R^3$)($R^4$)($R^5$) is directly attached to Ring A As used herein, the reference to carboxylic acid mimic or bioisostere includes groups as defined in The Practice of Medicinal Chemistry, Wermuth C. G. Ed.: Academic Press: New York, 1996, p 203. Particular examples of such groups include —$SO_3H$, $S(O)_2NHR^{13}$, —$S(O)_2NHC(O)R^{13}$, —$CH_2S(O)_2R^{13}$, —$C(O)NHS(O)_2R^{13}$, —C(O)NHOH, —C(O)NHCN, —CH($CF_3$)OH, C($CF_3$)$_2$OH, —P(O)(OH)$_2$ and groups of sub-formula (a)-(i') below

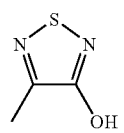
(a)

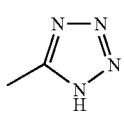
(b)

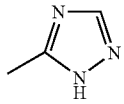
(c)

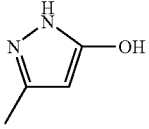
(d)

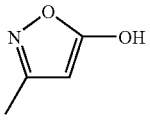
(e)

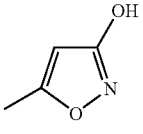
(f)

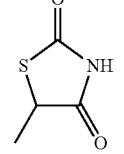
(g)

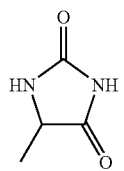
(h)

-continued

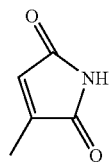
(i)

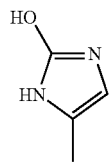
(j)

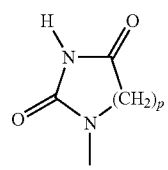
(k)

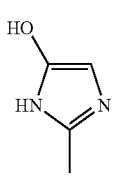
(l)

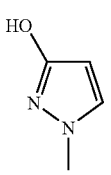
(m)

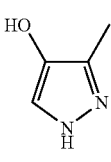
(n)

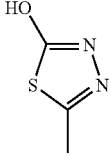
(o)

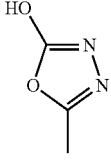
(p)

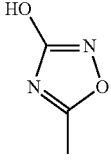
(q)

-continued
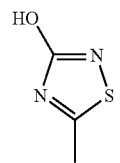 (r)
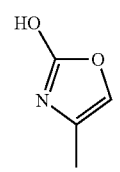 (s)
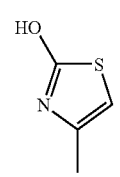 (t)
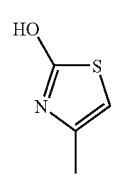 (u)
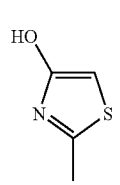 (v)
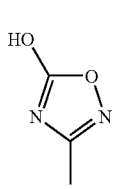 (w)
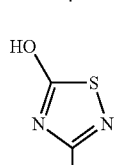 (x)
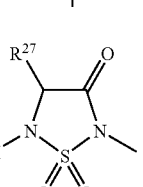 (y)
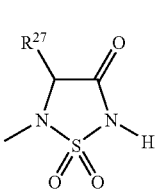 (z)
-continued
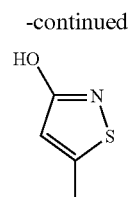 (a')
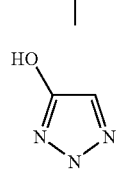 (b')
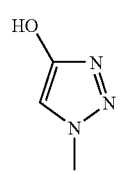 (c')
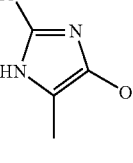 (d')
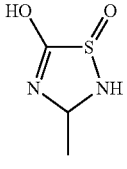 (e')
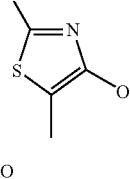 (f')
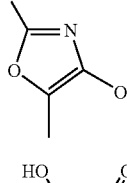 (g')
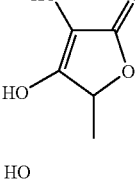 (h')
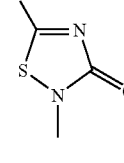 (i')
wherein $R^{13}$ is (1-6C)alkyl, aryl or heteroaryl; and $R^{27}$ is hydrogen or (1-4C)alkyl. It will be understood that in the above sub-formulae (a) to (i'), keto-enol tautomerism may be possible and that the sub-formulae (a) to (i') should be taken to encompass all tautomers thereof.

Examples of (1-6C)alkyl include methyl, ethyl, propyl, isopropyl, t-butyl, pentyl, iso-pentyl, 1-2-dimethylpropyl and hexyl; examples of (1-6C)alkoxy include methoxy, ethoxy, propoxy, isopropoxy, tert-butoxy and pentoxy; examples of (1-6C)alkylthio include methylthio, ethylthio, propylthio, isopropylthio and butylthio; examples of halo are chloro, bromo, iodo and fluoro; examples of trihalomethyl include trifluoromethyl.

A compound of formula (I) may form stable acid or basic salts, and in such cases administration of a compound as a salt may be appropriate, and pharmaceutically acceptable salts may be made by conventional methods such as those described following.

Suitable pharmaceutically-acceptable salts include acid addition salts such as methanesulfonate, tosylate, α-glycerophosphate, fumarate, hydrochloride, citrate, maleate, acetate, tartrate and (less preferably) hydrobromide. Also suitable are salts formed with phosphoric and sulfuric acid. In another aspect suitable salts are base salts such as those formed by group I (alkali) or group II (alkaline earth) metals, an organic amine salt for example triethylamine, diethanolamine, morpholine, N-methylpiperidine, N-ethylpiperidine, procaine, dibenzylamine, N,N-dibenzylethylamine, tris-(2-hydroxyethyl)amine, N-methyl d-glucamine and amino acids such as lysine. There may be more than one cation or anion depending on the number of charged functions and the valency of the cations or anions.

However, to facilitate isolation of the salt during preparation, salts which are less soluble in the chosen solvent may be preferred whether pharmaceutically-acceptable or not.

Within the present invention it is to be understood that a compound of the formula (I) or a salt thereof may exhibit the phenomenon of tautomerism and that the formulae drawings within this specification can represent only one of the possible tautomeric forms. It is to be understood that the invention encompasses any tautomeric form which inhibits DGAT1 activity and is not to be limited merely to any one tautomeric form utilised within the formulae drawings.

Various forms of prodrugs are known in the art. For examples of such prodrug derivatives, see:
a) Design of Prodrugs, edited by H. Bundgaard, (Elsevier, 1985) and Methods in Enzymology, Vol. 42, p. 309-396, edited by K. Widder, et al. (Academic Press, 1985);
b) A Textbook of Drug Design and Development, edited by Krogsgaard-Larsen and H. Bundgaard, Chapter 5 "Design and Application of Prodrugs", by H. Bundgaard p. 113-191 (1991);
c) H. Bundgaard, Advanced Drug Delivery Reviews, 8, 1-38 (1992);
d) H. Bundgaard, et al., Journal of Pharmaceutical Sciences, 77, 285 (1988); and
e) N. Kakeya, et al., Chem Pharm Bull, 32, 692 (1984).

Examples of such prodrugs are in vivo cleavable esters of a compound of the invention. An in vivo cleavable ester of a compound of the invention containing a carboxy group is, for example, a pharmaceutically-acceptable ester which is cleaved in the human or animal body to produce the parent acid. Suitable pharmaceutically-acceptable esters for carboxy include (1-6C)alkyl esters, for example methyl or ethyl; (1-6C)alkoxymethyl esters, for example methoxymethyl; (1-6C)alkanoyloxymethyl esters, for example pivaloyloxymethyl; phthalidyl esters; (3-8C)cycloalkoxycarbonyloxy(1-6C)alkyl esters, for example 1-cyclohexylcarbonyloxyethyl; 1,3-dioxolan-2-ylmethyl esters, for example 5-methyl-1,3-dioxolan-2-ylmethyl; (1-6C)alkoxycarbonyloxyethyl esters, for example 1-methoxycarbonyloxyethyl; aminocarbonylmethyl esters and mono- or di-N-((1-6C)alkyl) versions thereof, for example N,N-dimethylaminocarbonylmethyl esters and N-ethylaminocarbonylmethyl esters; and may be formed at any carboxy group in the compounds of this invention. An in vivo cleavable ester of a compound of the invention containing a hydroxy group is, for example, a pharmaceutically-acceptable ester which is cleaved in the human or animal body to produce the parent hydroxy group. Suitable pharmaceutically acceptable esters for hydroxy include (1-6C)alkanoyl esters, for example acetyl esters; and benzoyl esters wherein the phenyl group may be substituted with aminomethyl or N-substituted mono- or di-(1-6C)alkyl aminomethyl, for example 4-aminomethylbenzoyl esters and 4-N,N-dimethylaminomethylbenzoyl esters.

It will be appreciated by those skilled in the art that certain compounds of formula (I) contain asymmetrically substituted carbon atoms, and accordingly may exist in, and be isolated in, optically-active and racemic forms. Some compounds may exhibit polymorphism. It is to be understood that the present invention encompasses any racemic, optically-active, polymorphic or stereoisomeric form, or mixtures thereof, which form possesses properties useful in the inhibition of DGAT1 activity, it being well known in the art how to prepare optically-active forms (for example, by resolution of the racemic form by recrystallization techniques, by synthesis from optically-active starting materials, by chiral synthesis, by enzymatic resolution, by biotransformation, or by chromatographic separation using a chiral stationary phase) and how to determine efficacy for the inhibition of DGAT1 activity by the standard tests described hereinafter.

It is also to be understood that certain compounds of the formula (I) and salts thereof can exist in solvated as well as unsolvated forms such as, for example, hydrated forms. It is to be understood that the invention encompasses all such solvated forms which inhibit DGAT1 activity, including solvated forms of salts of compounds of formula (I). Therefore in another aspect, there is provided a compound of formula (I) and salts and solvates thereof. A particular example of a solvate is the acetic acid solvate of Example 1.

As stated before, we have discovered a range of compounds that have good DGAT1 inhibitory activity. They have good physical and/or pharmacokinetic properties in general. The following compounds possess preferred pharmaceutical and/or physical and/or pharmacokinetic properties.

Particular aspects of the invention comprise a compound of formula (I), or a salt, particularly a pharmaceutically-acceptable salt thereof, wherein any of the groups/substituents mentioned above have values defined hereinbefore, or any of the following values (which may be used where appropriate with any of the definitions, aspects and embodiments disclosed hereinbefore or hereinafter):

In one embodiment of the invention are provided compounds of formula (I), in an alternative embodiment are provided pharmaceutically-acceptable salts of compounds of formula (I). In a further embodiment are provided pro-drugs of compounds of formula (I). In a still further embodiment are provided pharmaceutically-acceptable salts of pro-drugs of compounds of formula (I).

In one aspect, $R^1$ is hydrogen. In another aspect, $R^1$ is methyl. In a further aspect, $R^1$ is trifluoromethyl.

In one aspect, $R^2$ is hydrogen. In another aspect, $R^2$ is chloro. In a further aspect, $R^2$ is fluoro.

In one aspect, $R^3$ is carboxy. In another aspect, $R^3$ is a carboxylic acid mimic or bioisostere.

In one aspect, $R^4$ is hydrogen. In another aspect, $R^4$ is methyl.

In one aspect, $R^5$ is hydrogen. In another aspect, $R^5$ is methyl.
In another aspect, $R^4$ is methyl and $R^5$ is hydrogen.
In a further aspect, both $R^4$ and $R^5$ are hydrogen.
In one aspect Ring A is (7C)bicycloalkanediyl.
In another aspect Ring A is (8C)bicycloalkanediyl.
In another aspect Ring A is (9C)bicycloalkanediyl.
In another aspect Ring A is (10C)bicycloalkanediyl.
In another aspect Ring A is (8-10C)bicycloalkanediyl.
In another aspect Ring A is (8-9C)bicycloalkanediyl (ie bicyclooctanediyl or bicyclononanediyl).
In another aspect Ring A is (8-12C)tricycloalkanediyl.
In another aspect Ring A is adamantyl.
In a further aspect, both $R^1$ and $R^2$ are hydrogen.
In one aspect n is 0.
In another aspect n is 1.
In a further aspect of the invention there is provided a compound of formula (I) or a salt thereof, wherein:
$R^1$ is selected from hydrogen, methyl and trifluoromethyl;
$R^2$ is hydrogen, chloro or fluoro;
Ring A is (7-10C)bicycloalkanediyl;
$R^3$ is carboxy;
$R^4$ is hydrogen or methyl;
$R^5$ is hydrogen or methyl;
n is 0 or 1.
In a further aspect of the invention there is provided a compound of formula (I) or a salt thereof, wherein:
$R^1$ is selected from hydrogen, methyl and trifluoromethyl;
$R^2$ is hydrogen, chloro or fluoro;
Ring A is (7-10C)bicycloalkanediyl;
$R^3$ is carboxy;
$R^4$ is hydrogen or methyl;
$R^5$ is hydrogen or methyl;
n is 1.
In a further aspect of the invention there is provided a compound of formula (I) or a salt thereof, wherein:
$R^1$ is selected from hydrogen, methyl and trifluoromethyl;
$R^2$ is hydrogen, chloro or fluoro;
Ring A is (7-10C)bicycloalkanediyl;
$R^3$ is carboxy;
$R^4$ is hydrogen or methyl;
$R^5$ is hydrogen;
n is 1.
In a further aspect of the invention there is provided a compound of formula (I) or a salt thereof, wherein:
$R^1$ is selected from hydrogen, methyl and trifluoromethyl;
$R^2$ is hydrogen, chloro or fluoro;
Ring A is (7-10C)bicycloalkanediyl;
$R^3$ is carboxy;
$R^4$ is hydrogen or methyl;
$R^5$ is hydrogen;
n is 1.
In a further aspect of the invention there is provided a compound of formula (I) or a salt thereof, wherein:
$R^1$ is hydrogen;
$R^2$ is hydrogen;
Ring A is (7-10C)bicycloalkanediyl or (8-12C)tricycloalkanediyl;
$R^3$ is carboxy;
$R^4$ is hydrogen or methyl;
$R^5$ is hydrogen;
n is 0 or 1.
In a further aspect of the invention there is provided a compound of formula (I) or a salt thereof, wherein:
$R^1$ is hydrogen;
$R^2$ is hydrogen;
Ring A is (8-9C)bicycloalkanediyl or adamantyl;
$R^3$ is carboxy;
$R^4$ is hydrogen or methyl;
$R^5$ is hydrogen;
n is 0 or 1.

Preferred compounds of the invention are each of the Examples, or a salt, particularly a pharmaceutically-acceptable salt thereof, each of which provides a further independent aspect of the invention. In further aspects, the present invention also comprises any two or more compounds of the Examples or a pharmaceutically-acceptable salt, thereof.

Preferred compounds of the invention are any one of the following, or their salts:

{4-[4-(4-amino-7,7-dimethyl-7H-pyrimido[4,5-b][1,4]oxazin-6-yl)phenyl]bicyclo[2.2.2]oct-1-yl}acetic acid; and/or {3-[4-(4-amino-7,7-dimethyl-7H-pyrimido[4,5-b][1,4]oxazin-6-yl)phenyl]-1-adamantyl}acetic acid;

3-[4-(4-amino-7,7-dimethyl-7H-pyrimido[4,5-b][1,4]oxazin-6-yl)phenyl]adamantane-1-carboxylic acid;

2-{4-[4-(4-amino-7,7-dimethyl-7H-pyrimido[4,5-b][1,4]oxazin-6-yl)phenyl]bicyclo[2.2.2]oct-1-yl}propanoic acid;

{5-[4-(4-amino-7,7-dimethyl-7H-pyrimido[4,5-b][1,4]oxazin-6-yl)phenyl]bicyclo[3.2.2]non-1-yl}acetic acid;

4-[4-(4-amino-7,7-dimethyl-7H-pyrimido[4,5-b][1,4]oxazin-6-yl)phenyl]bicyclo[2.2.2]octane-1-carboxylic acid.

DETAILED DESCRIPTION OF THE DRAWINGS

FIG. 1 shows the x-ray powder diffraction pattern of an isolated non-hydrate crystalline form of the compound of Example 1.

FIG. 2 shows the x-ray powder diffraction pattern of an isolated crystalline solvate of the compound of Example 1, wherein the solvate contains approximately a 1:1 ratio of acetic acid to compound.

PROCESS

A compound of formula (I) and its pharmaceutically-acceptable salts may be prepared by any process known to be applicable to the preparation of chemically related compounds. Such processes, when used to prepare a compound of the formula (I), or a pharmaceutically-acceptable salt thereof, are provided as a further feature of the invention.

In a further aspect the present invention also provides that the compounds of the formula (I) and pharmaceutically-acceptable salts thereof, can be prepared by a process a) as follows (wherein all variables are as hereinbefore defined for a compound of formula (I), or are protected versions thereof, unless otherwise stated):

a) reaction of a compound of formula (II), wherein $R^3$ is an ester group, for example methoxycarbonyl;

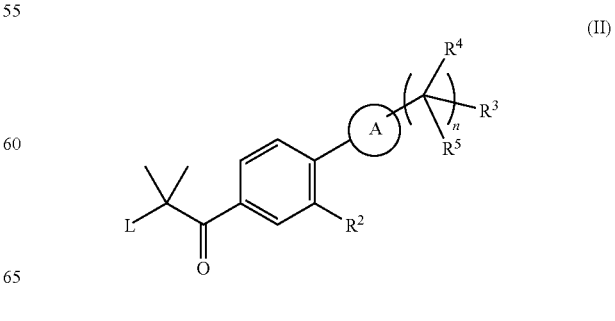

with a compound of formula (III) or a salt thereof,

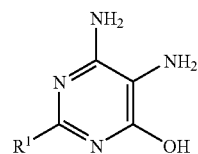

(III)

wherein L is a leaving group such as bromo and thereafter if necessary:

i) hydrolysing the ester $R^3$ to the corresponding carboxylic acid; and/or ii) forming a salt.

It will be understood that the compounds of formula (I), or salts thereof may be isolated as a solvate by techniques known in the art, see also Example 1. Therefore forming a solvate comprises an optional final step of the above process.

Process a): The cyclisation reaction between compounds of the formula (II) and (III) may be carried out by heating in a suitable solvent such as aqueous ethanol, preferably in the presence of a catalyst, for example hydrochloric acid. Intermediates of formula (II) may be obtained through acylation of a compound of formula (IV) with, for example, 2-bromoisobutyryl bromide in the presence of a catalyst such as aluminium chloride.

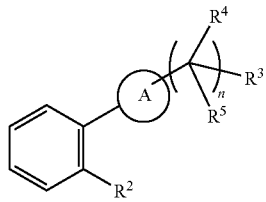

(IV)

Compounds of formula (IV) in which $R^4$=methyl and $R^5$=H may be obtained by alkylation of the corresponding compounds where $R^4$=H using, for example, iodomethane in the presence of a suitable base such as lithium diisopropylamide. Compounds of formula (IV) in which $R^4$ and $R^5$ are both methyl may be made similarly by two sequential alkylation reactions.

Compounds of formula (IV) in which $R^3$ is an ester and $R^4$=$R^5$=H and n=1 may be obtained by a homologation of compounds of formula (V) by conversion into the acid chloride followed by reaction with trimethylsilyldiazomethane and then by methanol. Alternatively, other homologation procedures known in the art may be employed, for example conversion of compounds of formula (V) or their corresponding esters into the corresponding N-methoxy-N-methylamides, followed by reduction, for example with lithium aluminium hydride, to the corresponding aldehydes. These aldehydes are then subjected to Wittig reactions to give enol ethers of formula (VI) which can then be oxidised, for example with pyridinium chlorochromate to compounds of formula (IV) in which $R^3$ is an ester and $R^4$=$R^5$=H. A further homologation procedure is the reduction of a compound of formula (V) or its ester to the corresponding alcohol, conversion of the alcohol into leaving groups, for example by tosylation (tosyl=p-toluenesulfonyl), followed by displacement by cyanide to give a nitrile of formula (VII) which may be hydrolysed and esterified by standard methods. This process is illustrated in Example 7.

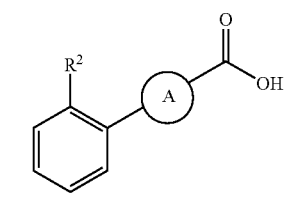

(V)

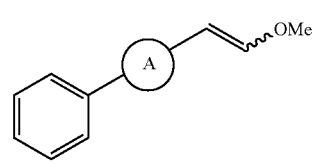

(VI)

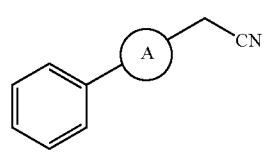

(VII)

Compounds of formula (V) in which $R^2$ is hydrogen and ring A is bicyclo[2.2.2]octane-1,4-diyl may be prepared as described by N. B Chapman, S. Sotheeswaran and K. J. Toyne *J. Org. Chem.*, 1970, 35, (4), 917, according to the reaction sequence shown in Scheme 1, followed by ester hydrolysis:

Scheme 1

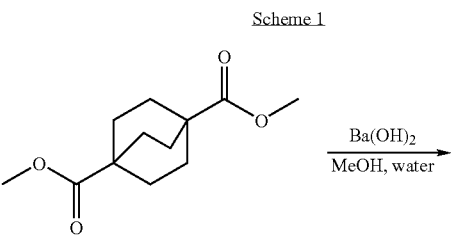

(VIII)

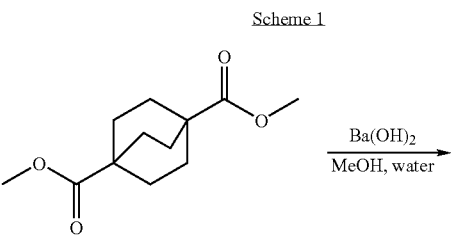

The diester bicyclo-octane (VIII) may be made by a variety of methods, for example according to J. Org. Chem., 1970, 35, (4), 917 (see Scheme 2), or according to Synthesis 1996, p 71 (see Scheme 3).

Scheme 2

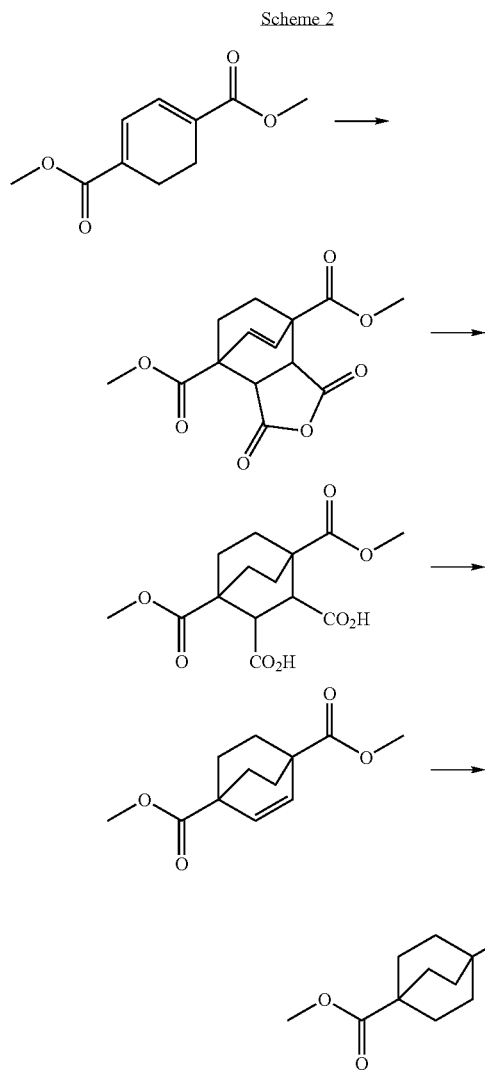

Scheme 3

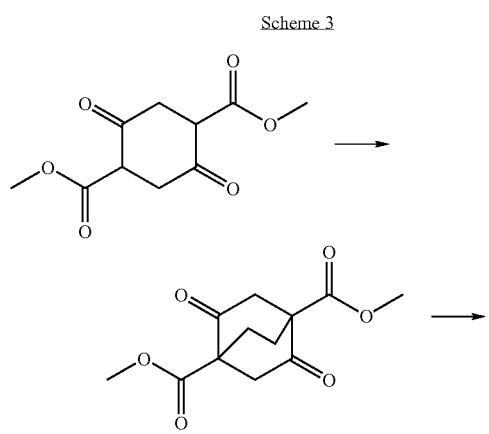

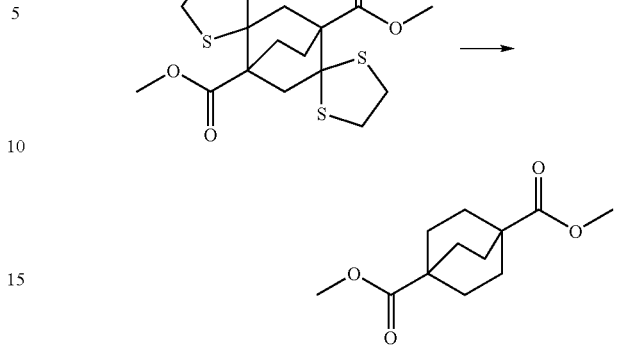

Alternatively, compounds of formula (V) in which $R^2$ is hydrogen may be made according to the process shown in Scheme 4, or analogously thereto (for example using modifications of the conditions given in Scheme 4, such as alternative hydrogenation catalysts (such as palladium on carbon) or alternative reagents to introduce the triflate (ie trifluoromethanesulfonate) group (such as trifluoromethanesulfonic anhydride).

Scheme 4

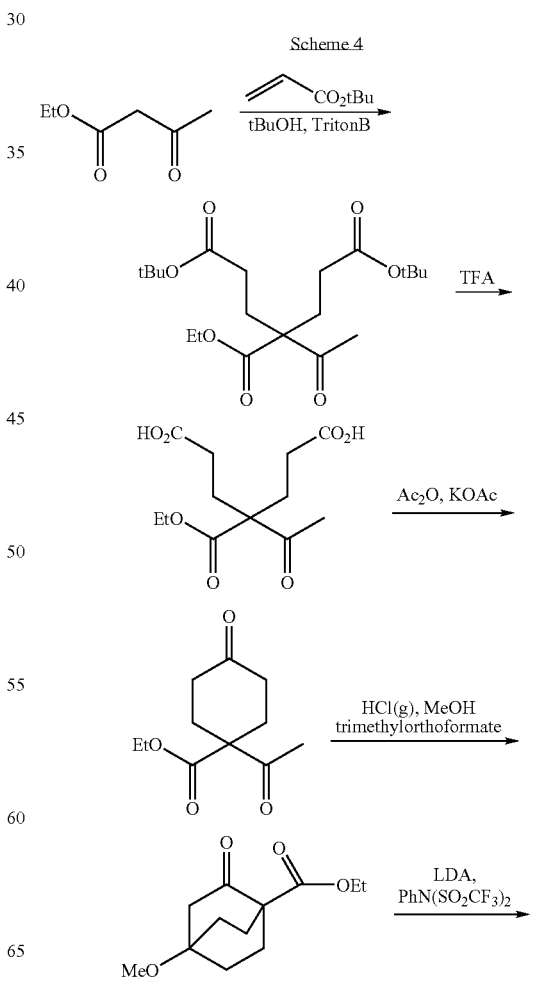

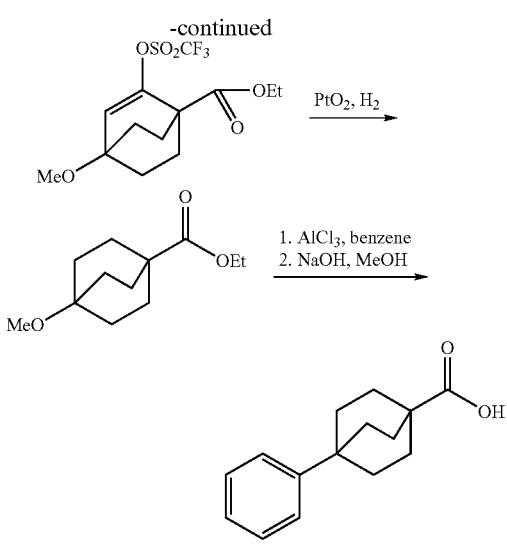

[LDA = lithium diisopropylamide, Ac = acetate (-C(O)Me), TFA = trifluoroacetic acid].

Alternatively, compounds of formula (V), wherein R[2] is hydrogen, chloro or fluoro may be made as their ester derivative according to the process shown in Scheme 5, or analogously thereto.

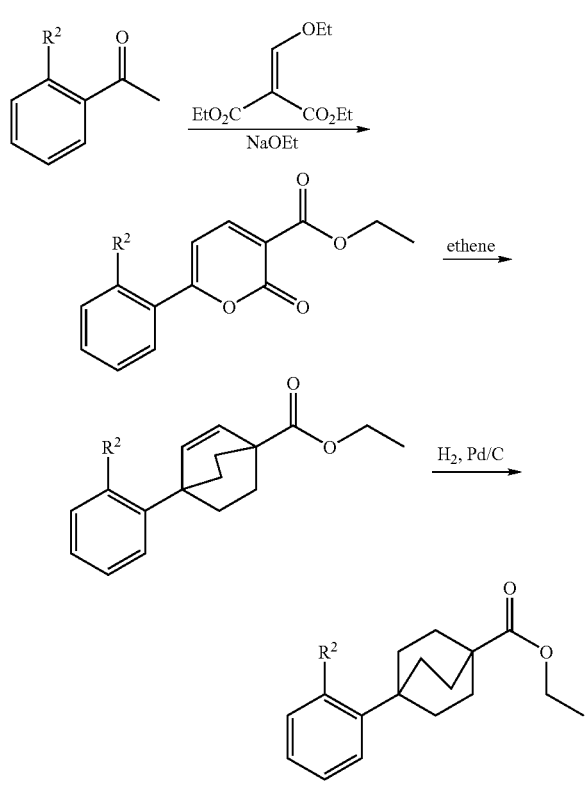

Compounds of formula (V) in which ring A is other than bicyclo[2.2.2]octane-1,4-diyl may be prepared by directly analogous processes. Suitable methods for preparing such compounds are also found in the accompanying examples.

If not commercially available, the necessary starting materials for the procedures such as those described above may be made by procedures which are selected from standard organic chemical techniques, techniques which are analogous to the synthesis of known, structurally similar compounds, techniques which are described or illustrated in the references given above, or techniques which are analogous to the above described procedure or the procedures described in the examples. The reader is further referred to Advanced Organic Chemistry, 5th Edition, by Jerry March and Michael Smith, published by John Wiley & Sons 2001, for general guidance on reaction conditions and reagents.

It will be appreciated that some intermediates to compounds of the formula (I) are also novel and these are provided as separate independent aspects of the invention. In particular, compounds of formula (II) form a further aspect of the invention. In another aspect of the invention, there is provided compounds of formula (IV). In one embodiment of this aspect is provided methyl (4-phenylbicyclo[2.2.2]oct-1-yl)acetate.

It will also be appreciated that in some of the reactions mentioned herein it may be necessary/desirable to protect any sensitive groups in compounds. The instances where protection is necessary or desirable are known to those skilled in the art, as are suitable methods for such protection. Conventional protecting groups may be used in accordance with standard practice (for illustration see T. W. Greene, Protective Groups in Organic Synthesis, John Wiley and Sons, 1991).

Protecting groups may be removed by any convenient method as described in the literature or known to the skilled chemist as appropriate for the removal of the protecting group in question, such methods being chosen so as to effect removal of the protecting group with minimum disturbance of groups elsewhere in the molecule.

Thus, if reactants include, for example, groups such as amino, carboxy or hydroxy it may be desirable to protect the group in some of the reactions mentioned herein.

Examples of a suitable protecting group for a hydroxy group is, for example, an acyl group, for example an alkanoyl group such as acetyl, an aroyl group, for example benzoyl, a silyl group such as trimethylsilyl or an arylmethyl group, for example benzyl. The deprotection conditions for the above protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium or sodium hydroxide. Alternatively a silyl group such as trimethylsilyl or SEM may be removed, for example, by fluoride or by aqueous acid; or an arylmethyl group such as a benzyl group may be removed, for example, by hydrogenation in the presence of a catalyst such as palladium-on-carbon.

A suitable protecting group for an amino group is, for example, an acyl group, for example an alkanoyl group such as acetyl, an alkoxycarbonyl group, for example a methoxycarbonyl, ethoxycarbonyl or tert-butoxycarbonyl group, an arylmethoxycarbonyl group, for example benzyloxycarbonyl, or an aroyl group, for example benzoyl. The deprotection conditions for the above protecting groups necessarily vary with the choice of protecting group. Thus, for example, an acyl group such as an alkanoyl or alkoxycarbonyl group or an aroyl group may be removed for example, by hydrolysis with a suitable base such as an alkali metal hydroxide, for example lithium or sodium hydroxide. Alternatively an acyl group such as a t-butoxycarbonyl group may be removed, for example, by treatment with a suitable acid as hydrochloric, sulfuric or phosphoric acid or trifluoroacetic acid and an arylmethoxycarbonyl group such as a benzyloxycarbonyl group may be removed, for example, by hydrogenation over a catalyst such as palladium-on-carbon, or by treatment with a Lewis acid for example boron tris(trifluoroacetate). A suitable alternative protecting group for a primary amino group is, for example, a phthaloyl group which may be removed by treatment with an alkylamine, for example dimethylaminopropylamine or 2-hydroxyethylamine, or with hydrazine.

A suitable protecting group for a carboxy group is, for example, an esterifying group, for example a methyl or an ethyl group which may be removed, for example, by hydrolysis with a base such as sodium hydroxide, or for example a t-butyl group which may be removed, for example, by treatment with an acid, for example an organic acid such as trifluoroacetic acid, or for example a benzyl group which may be removed, for example, by hydrogenation over a catalyst such as palladium-on-carbon.

Resins may also be used as a protecting group.

The protecting groups may be removed at any convenient stage in the synthesis using conventional techniques well known in the chemical art, or they may be removed during a later reaction step or work-up.

The skilled organic chemist will be able to use and adapt the information contained and referenced within the above references, and accompanying Examples therein and also the examples herein, to obtain necessary starting materials, and products.

The removal of any protecting groups and the formation of a pharmaceutically-acceptable salt are within the skill of an ordinary organic chemist using standard techniques. Furthermore, details on the these steps has been provided hereinbefore.

When an optically active form of a compound of the invention is required, it may be obtained by carrying out one of the above procedures using an optically active starting material (formed, for example, by asymmetric induction of a suitable reaction step), or by resolution of a racemic form of the compound or intermediate using a standard procedure, or by chromatographic separation of diastereoisomers (when produced). Enzymatic techniques may also be useful for the preparation of optically active compounds and/or intermediates.

Similarly, when a pure regioisomer of a compound of the invention is required, it may be obtained by carrying out one of the above procedures using a pure regioisomer as a starting material, or by resolution of a mixture of the regioisomers or intermediates using a standard procedure.

In a further aspect of the invention, there is provided a compound of formula (I) obtainable by a process as described hereinbefore or as shown in the Examples.

According to a further aspect of the invention there is provided a pharmaceutical composition which comprises a compound of formula (I) as defined hereinbefore or a pharmaceutically-acceptable salt thereof, in association with a pharmaceutically-acceptable excipient or carrier.

The compositions of the invention may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intramuscular or intramuscular dosing or as a suppository for rectal dosing). In general, compositions in a form suitable for oral use are preferred.

The compositions of the invention may be obtained by conventional procedures using conventional pharmaceutical excipients, well known in the art. Thus, compositions intended for oral use may contain, for example, one or more colouring, sweetening, flavouring and/or preservative agents.

Suitable pharmaceutically acceptable excipients for a tablet formulation include, for example, inert diluents such as lactose, sodium carbonate, calcium phosphate or calcium carbonate, granulating and disintegrating agents such as corn starch or algenic acid; binding agents such as starch; lubricating agents such as magnesium stearate, stearic acid or talc; preservative agents such as ethyl or propyl p-hydroxybenzoate, and anti-oxidants, such as ascorbic acid. Tablet formulations may be uncoated or coated either to modify their disintegration and the subsequent absorption of the active ingredient within the gastrointestinal tract, or to improve their stability and/or appearance, in either case, using conventional coating agents and procedures well known in the art.

Compositions for oral use may be in the form of hard gelatin capsules in which the active ingredient is mixed with an inert solid diluent, for example, calcium carbonate, calcium phosphate or kaolin, or as soft gelatin capsules in which the active ingredient is mixed with water or an oil such as peanut oil, liquid paraffin, or olive oil.

Aqueous suspensions generally contain the active ingredient in finely powdered form (for example micron or submicron particles) together with one or more suspending agents, such as sodium carboxymethylcellulose, methylcellulose, hydroxypropylmethylcellulose, sodium alginate, polyvinyl-pyrrolidone, gum tragacanth and gum acacia; dispersing or wetting agents such as lecithin or condensation products of an alkylene oxide with fatty acids (for example polyoxethylene stearate), or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives (such as ethyl or propyl p-hydroxybenzoate, anti-oxidants (such as ascorbic acid), colouring agents, flavouring agents, and/or sweetening agents (such as sucrose, saccharine or aspartame).

Oily suspensions may be formulated by suspending the active ingredient in a vegetable oil (such as arachis oil, olive oil, sesame oil or coconut oil) or in a mineral oil (such as liquid paraffin). The oily suspensions may also contain a thickening agent such as beeswax, hard paraffin or cetyl alcohol. Sweetening agents such as those set out above, and flavouring agents may be added to provide a palatable oral preparation. These compositions may be preserved by the addition of an anti-oxidant such as ascorbic acid.

Dispersible powders and granules suitable for preparation of an aqueous suspension by the addition of water generally contain the active ingredient together with a dispersing or wetting agent, suspending agent and one or more preservatives. Suitable dispersing or wetting agents and suspending agents are exemplified by those already mentioned above.

Additional excipients such as sweetening, flavouring and colouring agents, may also be present.

The pharmaceutical compositions of the invention may also be in the form of oil-in-water emulsions. The oily phase may be a vegetable oil, such as olive oil or arachis oil, or a mineral oil, such as for example liquid paraffin or a mixture of any of these. Suitable emulsifying agents may be, for example, naturally-occurring gums such as gum acacia or gum tragacanth, naturally-occurring phosphatides such as soya bean, lecithin, an esters or partial esters derived from fatty acids and hexitol anhydrides (for example sorbitan monooleate) and condensation products of the said partial esters with ethylene oxide such as polyoxyethylene sorbitan monooleate. The emulsions may also contain sweetening, flavouring and preservative agents.

Syrups and elixirs may be formulated with sweetening agents such as glycerol, propylene glycol, sorbitol, aspartame or sucrose, and may also contain a demulcent, preservative, flavouring and/or colouring agent.

The pharmaceutical compositions may also be in the form of a sterile injectable aqueous or oily suspension, which may be formulated according to known procedures using one or more of the appropriate dispersing or wetting agents and suspending agents, which have been mentioned above. A sterile injectable preparation may also be a sterile injectable solution or suspension in a non-toxic parenterally-acceptable diluent or solvent, for example a solution in 1,3-butanediol.

Compositions for administration by inhalation may be in the form of a conventional pressurised aerosol arranged to dispense the active ingredient either as an aerosol containing finely divided solid or liquid droplets. Conventional aerosol propellants such as volatile fluorinated hydrocarbons or hydrocarbons may be used and the aerosol device is conveniently arranged to dispense a metered quantity of active ingredient.

For further information on formulation the reader is referred to Chapter 25.2 in Volume 5 of Comprehensive Medicinal Chemistry (Corwin Hansch; Chairman of Editorial Board), Pergamon Press 1990.

The amount of active ingredient that is combined with one or more excipients to produce a single dosage form will necessarily vary depending upon the host treated and the particular route of administration. For example, a formulation intended for oral administration to humans will generally contain, for example, from 0.5 mg to 2 g of active agent compounded with an appropriate and convenient amount of excipients which may vary from about 5 to about 98 percent by weight of the total composition. Dosage unit forms will generally contain about 1 mg to about 500 mg of an active ingredient. For further information on Routes of Administration and Dosage Regimes the reader is referred to Chapter 25.3 in Volume 5 of Comprehensive Medicinal Chemistry (Corwin Hansch; Chairman of Editorial Board), Pergamon Press 1990.

According to a further aspect of the present invention there is provided a compound of formula (I) or a pharmaceutically acceptable salt thereof as defined hereinbefore for use in a method of treatment of the human or animal body by therapy.

We have found that compounds of the present invention inhibit DGAT1 activity and are therefore of interest for their blood glucose-lowering effects.

A further feature of the present invention is a compound of formula (I) or a pharmaceutically-acceptable salt thereof for use as a medicament.

Conveniently this is a compound of formula (I), or a pharmaceutically-acceptable salt thereof, for use as a medicament for producing an inhibition of DGAT1 activity in a warm-blooded animal such as a human being.

Particularly this is a compound of formula (I), or a pharmaceutically-acceptable salt thereof, for use as a medicament for treating diabetes mellitus and/or obesity in a warm-blooded animal such as a human being.

Thus according to a further aspect of the invention there is provided the use of a compound of formula (I), or a pharmaceutically-acceptable salt thereof in the manufacture of a medicament for use in the production of an inhibition of DGAT1 activity in a warm-blooded animal such as a human being.

Thus according to a further aspect of the invention there is provided the use of a compound of formula (I), or a pharmaceutically-acceptable salt thereof in the manufacture of a medicament for use in the treatment of diabetes mellitus and/or obesity in a warm-blooded animal such as a human being.

According to a further aspect of the invention there is provided a pharmaceutical composition which comprises a compound of formula (I) as defined hereinbefore or a pharmaceutically-acceptable salt thereof, in association with a pharmaceutically-acceptable excipient or carrier for use in producing an inhibition of DGAT1 activity in an warm-blooded animal, such as a human being.

According to a further aspect of the invention there is provided a pharmaceutical composition which comprises a compound of formula (I) as defined hereinbefore or a pharmaceutically-acceptable salt thereof, in association with a pharmaceutically-acceptable excipient or carrier for use in the treatment of diabetes mellitus and/or obesity in an warm-blooded animal, such as a human being.

According to a further feature of the invention there is provided a method for producing an inhibition of DGAT1 activity in a warm-blooded animal, such as a human being, in need of such treatment which comprises administering to said animal an effective amount of a compound of formula (I) or a pharmaceutically-acceptable salt thereof as defined hereinbefore.

According to a further feature of the invention there is provided a method of treating diabetes mellitus and/or obesity in a warm-blooded animal, such as a human being, in need of such treatment which comprises administering to said animal an effective amount of a compound of formula (I) or a pharmaceutically-acceptable salt thereof as defined hereinbefore.

As stated above the size of the dose required for the therapeutic or prophylactic treatment of a particular disease state will necessarily be varied depending on the host treated, the route of administration and the severity of the illness being treated. For example a daily dose in the range of 1-50 mg/kg may be employed. However the daily dose will necessarily be varied depending upon the host treated, the particular route of administration, and the severity of the illness being treated. Accordingly the optimum dosage may be determined by the practitioner who is treating any particular patient.

As stated above compounds defined in the present invention are of interest for their ability to inhibit the activity of DGAT1. A compound of the invention may therefore be useful for the prevention, delay or treatment of a range of disease states including diabetes mellitus, more specifically type 2 diabetes mellitus (T2DM) and complications arising there from (for example retinopathy, neuropathy and nephropathy), impaired glucose tolerance (IGT), conditions of impaired fasting glucose, metabolic acidosis, ketosis, dysmetabolic syndrome, arthritis, osteoporosis, obesity and obesity related disorders, (which include peripheral vascular disease, (including intermittent claudication), cardiac failure and certain cardiac myopathies, myocardial ischaemia, cerebral ischaemia and reperfusion, hyperlipidaemias, atherosclerosis, infertility and polycystic ovary syndrome); the compounds of the invention may also be useful for muscle weakness, diseases of the skin such as acne, Alzheimer's disease, various immunomodulatory diseases (such as psoriasis), HIV infection, inflammatory bowel syndrome and inflammatory bowel disease such as Crohn's disease and ulcerative colitis.

In particular, the compounds of the present invention are of interest for the prevention, delay or treatment of diabetes mellitus and/or obesity and/or obesity related disorders. In one aspect, the compounds of the invention are used for prevention, delay or treatment of diabetes mellitus. In another aspect, the compounds of the invention are used for prevention, delay or treatment of obesity. In a further aspect, the compounds of the invention are used for prevention, delay or treatment of obesity related disorders.

The inhibition of DGAT1 activity described herein may be applied as a sole therapy or in combination with one or more other substances and/or treatments for the indication being treated. Such conjoint treatment may be achieved by way of the simultaneous, sequential or separate administration of the individual components of the treatment. Simultaneous treatment may be in a single tablet or in separate tablets. For example such conjoint treatment may be beneficial in the treatment of metabolic syndrome [defined as abdominal obesity (as measured by waist circumference against ethnic and gender specific cut-points) plus any two of the following: hypertriglyceridemia (>150 mg/dl; 1.7 mmol/l); low HDLc (<40 mg/dl or <1.03 mmol/l for men and <50 mg/dl or 1.29 mmol/l for women) or on treatment for low HDL (high density lipoprotein); hypertension (SBP≧130 mmHg DBP≧85 mmHg) or on treatment for hypertension; and hyperglycemia (fasting plasma glucose≧100 mg/dl or 5.6 mmol/l or impaired glucose tolerance or pre-existing diabetes mellitus)—International Diabetes Federation & input from IAS/NCEP].

Such conjoint treatments may include the following main categories:
1) Anti-obesity therapies such as those that cause weight loss by effects on food intake, nutrient absorption or energy expenditure, such as orlistat, sibutramine and the like.
2) Insulin secretagogues including sulphonylureas (for example glibenclamide, glipizide), prandial glucose regulators (for example repaglinide, nateglinide);
3) Agents that improve incretin action (for example dipeptidyl peptidase IV inhibitors, and GLP-1 agonists);
4) Insulin sensitising agents including PPARgamma agonists (for example pioglitazone and rosiglitazone), and agents with combined PPARalpha and gamma activity;
5) Agents that modulate hepatic glucose balance (for example metformin, fructose 1,6 bisphosphatase inhibitors, glycogen phopsphorylase inhibitors, glycogen synthase kinase inhibitors, glucokinase activators);
6) Agents designed to reduce the absorption of glucose from the intestine (for example acarbose);
7) Agents that prevent the reabsorption of glucose by the kidney (SGLT inhibitors);
8) Agents designed to treat the complications of prolonged hyperglycaemia (for example aldose reductase inhibitors);
9) Anti-dyslipidaemia agents such as, HMG-CoA reductase inhibitors (eg statins); PPARα-agonists (fibrates, eg gemfibrozil); bile acid sequestrants (cholestyramine); cholesterol absorption inhibitors (plant stanols, synthetic inhibitors); bile acid absorption inhibitors (IBATi) and nicotinic acid and analogues (niacin and slow release formulations);
10) Antihypertensive agents such as, β-blockers (eg atenolol, inderal); ACE inhibitors (eg lisinopril); Calcium antagonists (eg. nifedipine); Angiotensin receptor antagonists (eg candesartan), αantagonists and diuretic agents (eg. furosemide, benzthiazide);
11) Haemostasis modulators such as, antithrombotics, activators of fibrinolysis and antiplatelet agents; thrombin antagonists; factor Xa inhibitors; factor VIIa inhibitors); antiplatelet agents (eg. aspirin, clopidogrel); anticoagulants (heparin and Low molecular weight analogues, hirudin) and warfarin;
12) Agents which antagonise the actions of glucagon; and
13) Anti-inflammatory agents, such as non-steroidal anti-inflammatory drugs (eg. aspirin) and steroidal anti-inflammatory agents (eg. cortisone).

In addition to their use in therapeutic medicine, compounds of formula (I) and their pharmaceutically-acceptable salts are also useful as pharmacological tools in the development and standardisation of in vitro and in vivo test systems for the evaluation of the effects of inhibitors of DGAT1 activity in laboratory animals such as cats, dogs, rabbits, monkeys, rats and mice, as part of the search for new therapeutic agents.

As indicated above, all of the compounds, and their corresponding pharmaceutically-acceptable salts, are useful in inhibiting DGAT1. The ability of the compounds of formula (I), and their corresponding pharmaceutically-acceptable acid addition salts, to inhibit DGAT1 may be demonstrated employing the following enzyme assay:

Human Enzyme Assay

The in vitro assay to identify DGAT1 inhibitors uses human DGAT1 expressed in insect cell membranes as the enzyme source (Proc. Natl. Acad. Sci. 1998, 95, 13018-13023). Briefly, sf9 cells were infected with recombinant baculovirus containing human DGAT1 coding sequences and harvested after 48 h. Cells were lysed by homogenisation and membranes isolated by centrifuging at 100,000 g for 1 h at 4° C. in 0.25M sucrose, 10 mM Tris HCl (tris(hydroxymethyl) aminomethane hydrochloride), 1 mM EDTA (ethylenediamine tetraacetic acid). The pellet containing the membrane fraction was collected, resuspended in buffer and stored at −80° C.

DGAT1 activity was assayed by a modification of the method described by Coleman (Methods in Enzymology 1992, 209, 98-102). Compound at 1-10 µM was incubated with 0.8 µg membrane protein, 5 mM $MgCl_2$, and 100 µM 1,2 dioleoyl-sn-glycerol in a total assay volume of 200 µL. The reaction was started by adding $^{14}C$ oleoyl coenzyme A (30 µM final concentration) and incubated at room temperature for 30 minutes. The reaction was stopped by adding 200 µL 2-propanol:heptane (7:1). Radioactive triolein product was separated into the organic phase by adding 300 µL heptane and 100 µL 0.1 M carbonate buffer pH 9.5. DGAT1 activity was quantified by counting aliquots of the upper heptane layer by liquid scintillography.

Using this assay the compounds generally show activity with $IC_{50}$<10 µM, such as <1 µM, particularly <100 nM, more particularly <50 nM. Example 1 showed an $IC_{50}$ of 19 nM and Example 4 showed an $IC_{50}$ of 40 nM.

Compounds of the invention, and particularly Example 1, may have advantageous pharmacokinetic properties as described hereinbefore. This may be illustrated, for example, by measuring the half-life of a compound, for examples in an animal such as a rat (for example Han Wistar rat). Compounds are administered orally, either singly or as a component of a cassette of up to five compounds. A typical dose would be between 2.5 and 5 mg/kg (5 ml/kg dose volume) formulated as a suspension in hydroxypropyl methyl cellulose (HPMC)/Tween (surfactant). Compound plasma levels are determined at 0.25, 0.5, 1, 2, 3, 6, 12 and 24 hours after dosing, with analysis performed by HPLC/mass spectrometry.

For example, Example 1 had a half life of 9.8 hours in this test.

The ability of the compounds of formula (I), and their corresponding pharmaceutically-acceptable acid salts, to inhibit DGAT1 may further be demonstrated employing the following whole cell assays 1) and 2):

1) Measurement of Triglyceride Synthesis in 3T3 Cells

Mouse adipocyte 3T3 cells were cultured to confluency in 6 well plates in new born calf serum containing media. Differentiation of the cells was induced by incubating in medium containing 10% foetal calf serum, 1 μg/mL insulin, 0.25 μM dexamethasone and 0.5 mM isobutylmethyl xanthine. After 48 h the cells were maintained in medium containing 10% foetal calf serum and 1 μg/mL insulin for a further 4-6 days. For the experiment, the medium was changed to serum-free medium and the cells pre-incubated with compound solubilised in DMSO (final concentration 0.1%) for 30 minutes. De novo lipogenesis was measured by the addition of 0.25 mM sodium acetate plus 1 μCi/mL $^{14}$C-sodium acetate to each well for a further 2 h (J. Biol. Chem., 1976, 251, 6462-6464). The cells were washed in phosphate buffered saline and solubilised in 1% sodium dodecyl sulfate. An aliquot was removed for protein determination using a protein estimation kit (Perbio) based on the method of Lowry (J. Biol. Chem., 1951, 193, 265-275). The lipids were extracted into the organic phase using a heptane:propan-2-ol:water (80:20:2) mixture followed by aliquots of water and heptane according to the method of Coleman (Methods in Enzymology, 1992, 209, 98-104). The organic phase was collected and the solvent evaporated under a stream of nitrogen. The extracts solubilised in iso-hexane:acetic acid (99:1) and lipids separated via normal phase high performance liquid chromatography (HPLC) using a Lichrospher diol-5, 4×250 mm column and a gradient solvent system of iso-hexane:acetic acid (99:1) and iso-hexane:propan-2-ol:acetic acid (85:15:1), flow rate of 1 mL/minute according to the method of Silversand and Haux (1997). Incorporation of radiolabel into the triglyceride fraction was analysed using a Radiomatic Flo-one Detector (Packard) connected to the HPLC machine.

2) Measurement of Triglyceride Synthesis in MCF7 Cells

Human mammary epithelial (MCF7) cells were cultured to confluency in 6 well plates in foetal calf serum containing media. For the experiment, the medium was changed to serum-free medium and the cells pre-incubated with compound solubilised in DMSO (final concentration 0.1%) for 30 minutes. De novo lipogenesis was measured by the addition of 50 μM sodium acetate plus 3 μCi/mL $^{14}$C-sodium acetate to each well for a further 3 h (J. Biol. Chem., 1976, 251, 6462-6464). The cells were washed in phosphate buffered saline and solubilised in 1% sodium dodecyl sulfate. An aliquot was removed for protein determination using a protein estimation kit (Perbio) based on the method of Lowry (J. Biol. Chem., 1951, 193, 265-275). The lipids were extracted into the organic phase using a heptane:propan-2-ol:water (80:20:2) mixture followed by aliquots of water and heptane according to the method of Coleman (Methods in Enzymology, 1992, 209, 98-104). The organic phase was collected and the solvent evaporated under a stream of nitrogen. The extracts solubilised in iso-hexane:acetic acid (99:1) and lipids separated via normal phase high performance liquid chromatography (HPLC) using a Lichrospher diol-5, 4×250 mm column and a gradient solvent system of iso-hexane:acetic acid (99:1) and iso-hexane:propan-2-ol:acetic acid (85:15:1), flow rate of 1 mL/minute according to the method of Silversand and Haux (J. Chromat. B, 1997, 703, 7-14). Incorporation of radiolabel into the triglyceride fraction was analysed using a Radiomatic Flo-one Detector (Packard) connected to the HPLC machine.

In the above other pharmaceutical composition, process, method, use and medicament manufacture features, the alternative and preferred embodiments of the compounds of the invention described herein also apply.

EXAMPLES

The invention will now be illustrated by the following Examples in which, unless stated otherwise:

(i) temperatures are given in degrees Celsius (° C.); operations were carried out at room or ambient temperature, that is, at a temperature in the range of 18-25° C. and under an atmosphere of an inert gas such as argon;

(ii) organic solutions were dried over anhydrous magnesium sulphate; evaporation of solvent was carried out using a rotary evaporator under reduced pressure (600-4000 Pascals; 4.5-30 mmHg) with a bath temperature of up to 60° C.;

(iii) Purification by chromatography generally refers to flash column chromatography, on silica unless otherwise stated. Column chromatography was generally carried out using prepacked silica cartridges (from 4 g up to 400 g) such as Redisep™ (available, for example, from Presearch Ltd, Hitchin, Herts, UK) or Biotage (Biotage UK Ltd, Hertford, Herts, UK), eluted using a pump and fraction collector system. Alternatively chromatography was carried out using ISOLUTE prepacked silica cartridges (10 g to 50 g) (available for, for example, from IST, Dyffryn Business Park), in this case elution and fraction collection was carried out manually.

(iv) in general, the course of reactions was followed by TLC and reaction times are given for illustration only;

(v) yields are given for illustration only and are not necessarily those which can be obtained by diligent process development; preparations were repeated if more material was required;

(vi) the structures of the end-products of the Formula (d) were confirmed by nuclear (generally proton) magnetic resonance (NMR) with a field strength (for proton) of 300 MHz (generally using a Varian Gemini 2000) or 400 MHz (generally using a Bruker Avance DPX400), unless otherwise stated, and mass spectral techniques; proton magnetic resonance chemical shift values were measured on the delta scale and peak multiplicities are shown as follows: s, singlet; d, doublet; t, triplet; m, multiplet; br, broad; q, quartet, quin, quintet;

using perdeuterio dimethyl sulphoxide (DMSO-$d_6$) as solvent, unless otherwise stated (vii) chemical symbols have their usual meanings; SI units and symbols are used;

(viii) solvent ratios are given in volume:volume (v/v) terms;

(ix) Mass spectra (MS) data were (unless stated otherwise) generated on an LCMS system where the HPLC (High Performance Liquid Chromatography) component comprised generally either a Agilent 1100 or Waters Alliance HT (2790 & 2795) equipment and was run on a Phemonenex Gemini C18 5 μm, 50×2 mm column (or similar) eluting with either acidic eluent (for example, using a gradient between 0-95% water/acetonitrile with 5% of a 1% formic acid in 50:50 water:acetonitrile (v/v) mixture; or using an equivalent solvent system with methanol instead of acetonitrile), or basic eluent (for example, using a gradient between 0-95% water/acetonitrile with 5% of a 0.1% 880 Ammonia in acetonitrile mixture); and the MS component comprised generally a Waters ZQ spectrometer. Chromatograms for Electrospray (ESI) positive and negative Base Peak Intensity, and UV Total Absorption Chromatogram from 220-300 nm, are generated and values for m/z are given; generally, only ions which indicate the parent mass are reported and unless otherwise stated the value quoted is $(M+H)^+$;

(x) GC-MS was carried out by one of the following methods a)i), a)ii), b)i) or b)ii):

a)
i) Waters GCT Premier Gas Chromatography-Mass Spectrometry (GC-MS) analysis method using electron impact ionisation (EI):

Gas Chromatography-Mass Spectrometry analysis was carried out on a Waters GCT Premier GC-MS system connected to a HP6890 GC oven fitted with an Agilent 7683B autosampler. The GC column was a DB-5MS of length 30 m, 0.25 mm i.d. with a film thickness of 0.25 μm (J & W Scientific, Folsom, Calif., USA). The sample was dissolved in methanol at ~1 mg/ml concentration and 1 μl injected at a split ratio of 30:1. The Helium carrier gas was set at a flow rate of 1.0 ml/min. The following temperatures were set: GC injector temperature 250° C., Oven Temperature initially at 50° C., Mass Spectrometer interface 250° C. and the ion source at 200° C. During analysis the GC oven temperature was held at 50° C. for 4 min. and then the temperature was ramped at 25° C./min. to 280° C. and then at a rate of 50 (C/min. to 320° C. and finally held for 2 min. The mass spectrometer used electron impact ionisation (70 eV) and scanned the mass range 40 to 800 amu in 0.2 seconds ii) Waters GCT Premier Gas Chromatography-Mass Spectrometry (GC-MS) analysis method using positive chemical ionisation (+CI):

Gas Chromatography-Mass Spectrometry analysis was carried out on a Waters GCT Premier GC-MS system connected to a HP6890 GC oven fitted with an Agilent 7683B autosampler. The GC column was a DB-5MS of length 30 m, 0.25 mm i.d. with a film thickness of 0.25 μm (J & W Scientific, Folsom, Calif., USA). The sample was dissolved in methanol at ~1 mg/ml concentration and 1 μl injected at a split ratio of 30:1. The Helium carrier gas was set at a flow rate of 1.0 ml/min. The following temperatures were set: GC injector temperature 250° C., Oven Temperature initially at 50° C., Mass Spectrometer interface 250° C. and the ion source at 200° C. During analysis the GC oven temperature was held at 50° C. for 2 min. and then the temperature was ramped at 25° C./min. to 280° C. and then at a rate of 50° C./min. to 320° C. and finally held for 4 min. Positive ion chemical ionisation (CI) was produced using Methane CI gas at a pressure of $2.7 \times 10^{-3}$ Pa. The mass spectrometer scanned the mass range 40 to 800 amu in 0.2 seconds.

b)
i) Gas Chromatography-Mass Spectrometry (GC-MS) analysis method using electron impact ionisation (EI) QP-2010:

Gas Chromatography-Mass Spectrometry analysis was carried out on a QP-2010 GC-MS system fitted with an AOC 20i autosampler and controlled by 'GCMS solutions' software, version 2.0 (Shimadzu, Milton Keynes, MK12 5RE, UK). The GC column was a DB-5MS of length 25 m, 0.32 mm i.d. with a film thickness of 0.52 μm (J & W Scientific, Folsom, Calif., USA). The sample was dissolved in methanol at ~1 mg/ml concentration and 1 μl injected at a split ratio of 10:1. The Helium carrier gas was set at a flow rate of 1.8 ml/min. The following temperatures were set: GC injector temperature 250° C., Oven Temperature initially at 50° C., Mass Spectrometer interface 320° C. and the ion source at 200° C. During analysis the GC oven temperature was held at 50° C. for 4 min. and then the temperature was ramped at 25° C./min. to 280° C. and then at a rate of 50° C./min. to 320° C. and finally held for 4 min. The mass spectrometer used electron impact ionisation (70 eV) and scanned the mass range 50 to 600 amu at a scan speed of 1250 amu/sec.

ii) Gas Chromatography-Mass Spectrometry (GC-MS) analysis method using positive chemical ionisation (+CI) QP-2010:

Gas Chromatography-Mass Spectrometry analysis was carried out on a QP-2010 GC-MS system fitted with an AOC 20i autosampler and controlled by 'GCMS solutions' software, version 2.0 (Shimadzu, Milton Keynes, MK12 5RE, UK). The GC column was a DB-5MS of length 25 m, 0.32 mm i.d. with a film thickness of 0.52 μm (J & W Scientific, Folsom, Calif., USA). The sample was dissolved in methanol at ~1 mg/ml concentration and 1 μl injected at a split ratio of 20:1. The Helium carrier gas was set at a flow rate of 1.9 ml/min. The following temperatures were set: GC injector temperature 250° C., Oven Temperature initially at 50° C., Mass Spectrometer interface 320° C. and the ion source at 200° C. During analysis the GC oven temperature was held at 50° C. for 4 min. and then the temperature was ramped at 25° C./min. to 280° C. and then at a rate of 50° C./min. to 320° C. and finally held for 4 min. Positive ion chemical ionisation (CI) was produced using Methane CI gas at a pressure of $2.7 \times 10^{-3}$ Pa. The mass spectrometer scanned the mass range 50 to 600 amu at a scan speed of 1250 amu/sec.

(xi) Solid Probe Mass Spectrometry analysis was carried out using electron impact ionisation (EI) QP-2010 according to the following method:

Mass Spectrometry analysis was carried out on a QP-2010 instrument using software, version 2.0 (Shimadzu, Milton Keynes, MK12 5RE, UK). The sample was dissolved in methanol at ~1 mg/ml concentration; the ion source was at 200° C. Sample was introduced into the mass spectrometer using a solid probe; the probe temperature was ramped from 50-350° C.

(xii) Suitable microwave reactors include "Smith Creator", "CEM Explorer", "Biotage Initiator sixty" and "Biotage Initiator eight".

(xiii) The following abbreviations may be used below or in the process section hereinbefore:

| | |
|---|---|
| Et$_2$O/ether | diethyl ether |
| DMF | dimethylformamide |
| DCM | dichloromethane |
| MeOH | methanol |
| EtOH | ethanol |
| H$_2$O | water |
| THF | tetrahydrofuran |
| DMSO | dimethylsulfoxide |
| EtOAc | ethyl acetate |
| PS-CDI | polymer supported carbonyldiimidazole |
| HCl | hydrochloric acid |
| TFA | trifluoroacetic acid |
| DME | dimethoxyethane |
| MeCN | acetonitrile |
| n-BuLi | n-butyl lithium |
| MTBE | methyl t-butyl ether |
| Eq | molar equivalent |
| v/w | volume per weight |

Example 1

{4-[4-(4-Amino-7,7-dimethyl-7H-pyrimido[4,5-b][1,4]oxazin-6-yl)phenyl]bicyclo[2.2.2]oct-1-yl}acetic acid

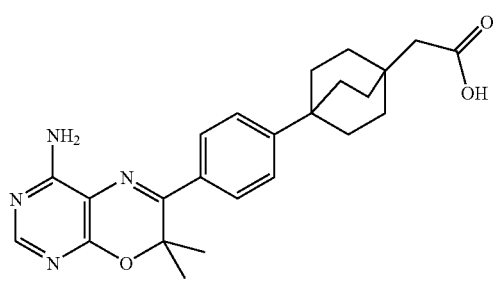

To a solution of methyl {4-[4-(4-amino-7,7-dimethyl-7H-pyrimido[4,5-b][1,4]oxazin-6-yl)phenyl]bicyclo[2.2.2]oct-1-yl}acetate (122 mg, 0.28 mmol) in MeOH (10 mL) and THF (5 mL) was added 2M NaOH (0.7 mL). The reaction mixture was stirred at ambient temperature overnight then further 2M NaOH (0.7 mL) was added and the reaction mixture heated to 50° C. for 5 hrs. The mixture was allowed to cool, the solvent was removed under reduced pressure and the residue was acidified to pH 2 with 2M HCl and the suspension filtered and dried. The product was purified on a basic reverse phase preparative HPLC system loading in NMP (~2 mL), water (~2 mL) and 1-2 drops of 0.88 ammonia, and eluting with 13-40% water (+1% $NH_3$)-MeCN, to provide the title compound as a solid, 40 mg (0.0952 mmol, 34%).

$^1$H NMR δ 1.61 (s, 6H), 1.62-1.65 (m, 6H), 1.77-1.80 (m, 6H), 1.94 (s, 2H), 6.90 (s, 2H), 7.39 (d, 2H), 7.64 (d, 2H), 7.95 (s, 1H); $CO_2H$ not seen; MS m/e $MH^+$ 421.

Example 1 was also prepared as follows:

To a solution of methyl {4-[4-(4-amino-7,7-dimethyl-7H-pyrimido[4,5-b][1,4]oxazin-6-yl)phenyl]bicyclo[2.2.2]oct-1-yl}acetate (Intermediate 10; 601 mg, 1.38 mmol) in MeOH (40 mL) and THF (40 mL) was added 2M NaOH solution (3.5 mL, 6.9 mmol). The reaction mixture was stirred at 60° C. overnight, the organic solvent was concentrated and the residue acidified with 2M HCl to pH 2. The suspension was filtered and the solid purified by reverse phase chromatography loading in DMSO/MeCN/$H_2O$ (7:2:1) with a few drops of concentrated ammonia solution and eluting 5-95% water (+0.5% $NH_3$)-MeCN. The title compound was isolated as a white solid (302 mg, 0.717 mmol, 52%.

Example 1 was crystallised from water by suspending the compound (141 mg) in water (7 mL) and stirring overnight at ambient temperature. The suspension was filtered and dried under vacuum at 50° C., to give the crystalline compound (127 mg) as a white solid. This crystalline form is believed to be an unhydrated form. The X-Ray Powder Diffraction pattern for this crystalline non-hydrate is shown in FIG. 1.

Example 1 was also isolated as an acetic acid solvate by the following method: {4-[4-(4-Amino-7,7-dimethyl-7H-pyrimido[4,5-b][1,4]oxazin-6-yl)phenyl]bicyclo[2.2.2]oct-1-yl}acetic acid (400 mg) was heated in glacial acetic acid (3 mL) at 135° C. (complete solution not obtained). The mixture was filtered and the filtrate allowed to cool. The resulting precipitate was filtered and dried under vacuum at 50° C. to provide the title compound as a white solid (125 mg). $^1$H NMR 1.61-1.65 (m, 6H), 1.61 (s, 6H), 1.79-1.83 (m, 6H), 1.92 (s, 3H), 2.06 (s, 2H), 6.90 (s, 1H), 7.40 (d, 2H), 7.64 (d, 2H), 7.95 (s, 1H), 11.91 (s, 1H). The X-Ray Powder Diffraction pattern for this crystalline solvate [which contains approximately a 1:1 ratio of acetic acid to compound] is shown in FIG. 2.

[The X-ray powder diffraction patterns were determined by mounting a sample of the crystalline material on Siemens single silicon crystal (SSC) wafer mounts and spreading out the sample into a thin layer with the aid of a microscope slide. The sample was spun at 30 revolutions per minute (to improve counting statistics) and irradiated with X-rays generated by a copper long-fine focus tube operated at 40 kV and 40 mA with a wavelength of 1.5406 Angstroms using a Bruker D5000 powder X-ray diffractometer (Bruker AXS, Banner Lane Coventry CV4 9 GH). The collimated X-ray source was passed through an automatic variable divergence slit set at V20 and the reflected radiation directed through a 2 mm antiscatter slit and a 0.2 mm detector slit. The sample was exposed for 1 second per 0.02 degree 2-theta increment (continuous scan mode) over the range 2 degrees to 40 degrees 2-theta in theta-theta mode. The instrument was equipped with a scintillation counter as detector. Control and data capture was by means of a Dell Optiplex 686 NT 4.0 Workstation operating with Diffrac+ software.

The skilled person is aware that an X-ray powder diffraction pattern may be obtained which has one or more measurement errors depending on measurement conditions (such as equipment, sample preparation or machine used). In particular, it is generally known that intensities in an X-ray powder diffraction pattern may fluctuate depending on measurement conditions and sample preparation. For example, the skilled person will realize that the relative intensity of peaks can be affected by, for example, grains above 30 microns in size and non-unitary aspect ratios, which may affect analysis of samples. The skilled person will also realize that the position of reflections can be affected by the precise height at which the sample sits in the diffractometer and the zero calibration of the diffractometer. The surface planarity of the sample may also have a small effect. Hence a person skilled in the art will appreciate that the diffraction pattern data presented herein is not to be construed as absolute (for further information see Jenkins, R & Snyder, R. L. 'Introduction to X-Ray Powder Diffractometry' John Wiley & Sons, 1996).]

Intermediate 1

Methyl {4-[4-(4-amino-7,7-dimethyl-7H-pyrimido[4,5-b][1,4]oxazin-6-yl)phenyl]bicyclo[2.2.2]oct-1-yl}acetate

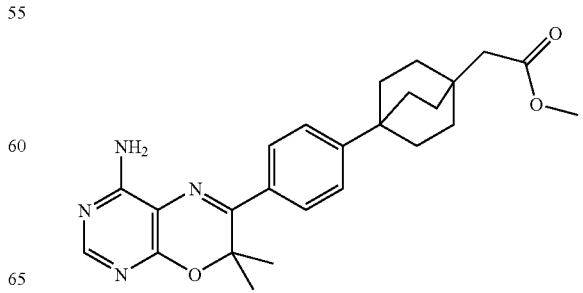

i) 4-Phenylbicyclo[2.2.2]octane-1-carboxylic acid

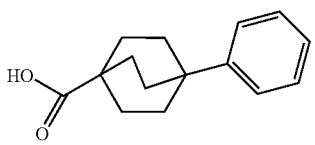

To a solution of methyl 4-phenylbicyclo[2.2.2]octane-1-carboxylate (obtained using the procedure described by N. B Chapman, S. Sotheeswaran and K. J. Toyne *J. Org. Chem.*, 1970, 35, (4), 917) (785 mg, 3.21 mmol) in methanol (60 mL) and THF (15 mL) was added 2M NaOH (8.0 mL, 16.06 mmol). The reaction mixture was allowed to stir at ambient temperature overnight, the methanol was removed by evaporation and the residue acidified to pH 2 with 2M HCl and then extracted with EtOAc (2×250 mL). The organic phase was washed with brine (50 mL) separated, dried (MgSO$_4$) and concentrated to leave a pale red solid, 682 mg (2.96 mmol, 92%);

$^1$H NMR δ 1.86 (s, 12H), 7.19-7.23 (m, 1H), 7.31-7.39 (m, 4H); MS m/e MH-229.

ii) Methyl (4-phenylbicyclo[2.2.2]oct-1-yl)acetate

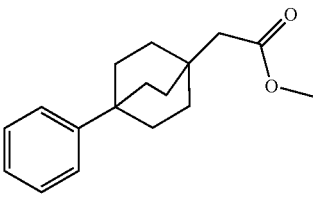

To an ice-water cooled solution of 4-phenylbicyclo[2.2.2]octane-1-carboxylic acid (479 mg, 2.07 mmol) in DCM (20 mL) was added DMF (2-3 drops) followed by oxalyl chloride (0.20 mL, 2.14 mmol). The reaction mixture was allowed to warm to ambient temperature overnight and then solvent was evaporated under reduced pressure to leave crude 4-phenylbicyclo[2.2.2]octane-1-carbonyl chloride which was used directly in the next stage.

This was redissolved in a 1:1 solution of MeCN and THF (10 mL) and added dropwise to an ice water cooled solution of 2M trimethylsilyldiazomethane (1.5 mL, 3.0 mmol) and triethylamine (0.40 mL, 2.60 mmol) in a 1:1 solution of MeCN and THF (20 mL). The resulting yellow reaction mixture was allowed to stir at 0° C. for 6 hrs and then allowed to stand at ambient temperature overnight. The solvent was removed under reduced pressure and the residue redissolved in EtOAc (100 mL) and washed with water (50 mL), NaHCO$_3$ (50 mL) and brine (50 mL). The organic phase was dried (MgSO$_4$), concentrated to leave a red brown gum. This was purified on a 12 g silica Crawford silica cartridge, eluting 0-10%-20% EtOAc using an Isco Companion, to give 2-diazo-1-(4-phenylbicyclo[2.2.2]oct-1-yl)ethanone (238 mg; 0.933 mmol, 45%) as a pale yellow gum which formed a cream solid on standing; $^1$H NMR (CDCl$_3$) δ1.82-1.91 (m, 12H), 5.38 (s, 1H), 7.15-7.21 (m, 2H), 7.29-7.31 (m, 4H); MS m/e MH$^+$ 255.

The diazoketone (0.238 mg, 0.933 mmol) was dissolved in methanol (10 mL) and placed in an ultrasound bath. A solution of silver benzoate (43 mg, 0.186 mmol, 0.2 eq) in triethylamine (0.52 mL, 3.73 mmol, 4 eq) was added dropwise and the mixture was sonicated for 1 hr. The methanol was removed by evaporation under reduced pressure and the residue dissolved in EtOAc (~50 mL) and washed with NaHCO$_3$ (40 mL), citric acid (2M; 40 mL), brine (40 mL) then dried (MgSO$_4$) and concentrated to leave a yellow oil (277 mg) which slowly formed a solid on standing; MS GC-MS EI m/e MH$^+$ 258. This material was taken on through directly to the next stage.

iii) Methyl {4-[4-(2-bromo-2-methylpropanoyl)phenyl]bicyclo[2.2.2]oct-1-yl}acetate

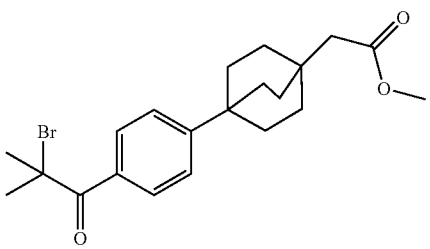

To an ice water cooled solution of methyl (4-phenylbicyclo[2.2.2]oct-1-yl)acetate (536 mg, 2.07 mmol) in DCM (30 mL) was added aluminum chloride (830 mg, 6.22 mmol) followed by the dropwise addition of 2-bromoisobutyryl bromide (0.25 mL, 2.07 mmol). The reaction mixture was allowed to stir at ~0° C. for 1 hr, then poured onto ice-water (~20 mL). The organic phase was separated and the aqueous phase washed with DCM (3×150 mL), the organic were combined, dried (MgSO$_4$) and concentrated to leave a yellow gum. This was purified on a 12 g silicyle silca cartridge, loading in DCM and eluting 0-10%-20% isohexane-EtOAc, to provide the title compound as a red solid, 648 mg (1.59 mmol, 77%); $^1$H NMR (CDCl$_3$) δ 1.65-1.69 (m, 6H), 1.84-1.88 (m, 6H), 2.03 (s, 6H), 2.18 (s, 2H), 3.66 (s, 3H), 7.36 (d, 2H), 8.09 (d, 2H); MS m/e MH$^+$ 377 (M-OMe).

iv) Methyl {4-[4-(4-amino-7,7-dimethyl-7H-pyrimido[4,5-b][1,4]oxazin-6-yl)phenyl]bicyclo[2.2.2]oct-1-yl}acetate To a solution of methyl {4-[4-(2-bromo-2-methylpropanoyl)phenyl]bicyclo[2.2.2]oct-1-yl}acetate (648 mg, 1.59 mmol) in absolute EtOH (15 mL) was added 5,6-diaminopyrimidin-4-ol (221 mg, 1.75 mmol) followed by 1M HCl (1.75 mL). The reaction mixture was heated under reflux overnight then allowed to cool to ambient temperature and evaporated to dryness. The residue was treated with 2M NaOH to adjust the pH to 11 and then the mixture was extracted into EtOAc (4×50 mL). The organic extracts were combined, dried (MgSO$_4$) and concentrated to leave the crude ester product. The aqueous phase was acidified with 2M HCl and then re extracted with EtOAc (2×100 mL), the organic extracts were combined, dried (MgSO$_4$) and concentrated to give some of the corresponding acid {4-[4-(4-amino-7,7-dimethyl-7H-pyrimido[4,5-b][1,4]oxazin-6-yl)phenyl]bicyclo[2.2.2]oct-1-yl}acetic acid (40 mg, 0.095 mmol, 6%). The ester was purified on a 12 g silica redisep cartridge dry loading the sample on celite and eluting with DCM-MeOH 0-2%-5% using an Isco Companion to provide the title compound as a solid 122 mg (0.281 mmol, 17.6%);

¹H NMR δ 1.58-1.63 (m, 14H), 1.78-1.83 (m, 7H), 2.16 (s, 2H), 3.59 (s, 3H), 6.90 (brs, 2H), 7.39 (d, 2H), 7.64 (d, 2H), 7.95 (s, 1H); MS m/e MH⁺ 435.

Intermediate 2

Ethyl 2-oxo-6-phenyl-2H-pyran-3-carboxylate

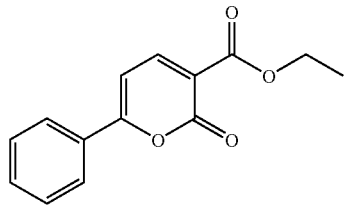

See A. von Kreisler et al, German Patent DE 1812906.

To a solution of sodium ethoxide (21% solution in ethanol; 116 mL, 358.33 mmol) in anhydrous DME (300 mL) was added diethyl (ethoxymethylene)malonate (66 mL, 325.75 mmol). The reaction mixture was heated to reflux and 1-phenylethanone (38 mL, 325.75 mmol) was added dropwise and heating maintained for 1 hr. The reaction mixture was allowed to cool to ambient temperature and added to a stirred solution of 5M HCl (500 mL) and the resulting yellow solution was extracted into ether (3×500 mL). The organic extracts were combined, washed with brine (300 mL), dried (MgSO₄) and concentrated to leave a red oil. Acetyl chloride (60 mL) was added followed by DMF (~2 mL) and the mixture was heated to 70° C. for 2 hrs, allowed to cool and then concentrated to leave a dark residue which formed a crystalline solid on standing. This was recrystallised from absolute EtOH (50 mL) to provide title compound as a yellow solid (49.16 g, 201.2 mmol, 62%) ¹H NMR (CDCl₃) δ 1.39 (3H, t), 4.39 (2H, q), 6.77 (1H, d), 7.47-7.53 (3H, m), 7.90 (2H, d), 8.29 (1H, d); GC-MS EI m/e M⁺ 244.

Intermediate 3

Ethyl 4-phenylbicyclo[2.2.2]oct-2-ene-1-carboxylate

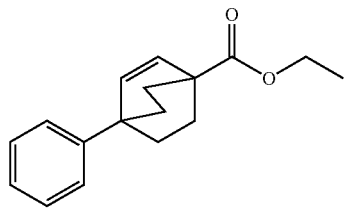

Ethyl 2-oxo-6-phenyl-2H-pyran-3-carboxylate (Intermediate 2; 49.1 g, 201.2 mmol) was dissolved in toluene and heated at 200° C. for 15 hrs at 75 bar pressure. The solvent was concentrated to leave a pale yellow gum (49 g). This was split into ~10 g portions and purified on a 330 g Crawford silica cartridge, loading in and eluting with 5% ether-95% isohexane, to provide the title compound as a colourless oil (26.4 g, 103 mmol, 51%); ¹H NMR (CDCl₃) δ 1.31 (3H, t), 1.58-1.61 (4H, m), 1.90-2.05 (4H, m), 4.23 (2H, q), 6.42 (1H, d), 6.59 (1H, d), 7.20-7.25 (1H, m), 7.32-7.40 (4H, m); GC-MS CI m/e MH⁺ 257.

Intermediate 4

Ethyl 4-phenylbicyclo[2.2.2]octane-1-carboxylate

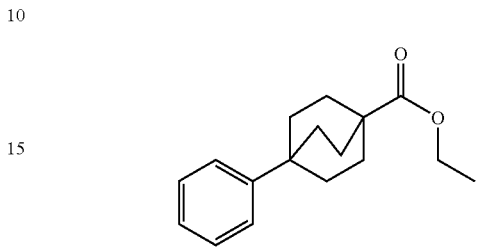

Ethyl 4-phenylbicyclo[2.2.2]oct-2-ene-1-carboxylate (Intermediate 3; 26.3 g, 102.5 mmol) in absolute ethanol (600 mL) and 10% Pt on carbon (2.4 mg) were stirred under a balloon of hydrogen at ambient temperature overnight. The reaction mixture was filtered and the solvent removed under reduced pressure to leave a colourless oil which rapidly formed a white solid (22.179 g, 85.96 mmol, 84%) ¹H NMR (CDCl₃) δ 1.25 (3H, t), 1.83-1.96 (12H, m), 4.12 (2H, q), 7.15-7.20 (1H, m), 7.28-7.31 (4H, m); GC-MS EI m/e M⁺ 258.

Intermediate 5

N-methoxy-N-methyl-1-phenylbicyclo[2.2.2]octane-4-carboxamide

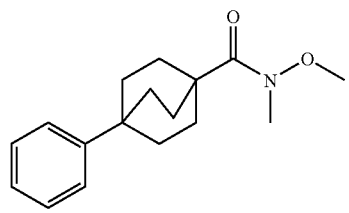

To a mixture of ethyl 1-phenylbicyclo[2.2.2]octane-4-carboxylate (Intermediate 4; 15 g, 58.06 mmol) and N,O-dimethylhydroxylamine hydrochloride (8.87 g, 89.99 mmol) in anhydrous THF (130 mL) cooled to −20° C. was added isopropylmagnesium chloride (2M solution in THF; 87 mL) dropwise over 30 mins maintaining the internal temp at −10° C. The mixture was stirred at −10° C. for 1 hr and then quenched by adding 20% ammonium chloride solution. The mixture was extracted into EtOAc (2×200 mL), the organic phase was separated and dried and evaporated to leave a white solid. This was purified on a 330 g Crawford silica cartridge, loading in DCM and eluting with 20-40% EtOAc-isohexane, to provide the title compound as a white solid (8.66 g, 31.67 mmol, 55%); ¹H NMR (CDCl₃) δ 1.75-1.90 (6H, m), 2.01-2.06 (6H, m), 3.19 (3H, s), 3.70 (3H, s), 7.15-7.20 (1H, m), 7.28-7.36 (4H, m); GC-MS EI+ m/e 243 (M-CH₂O), MH+ not seen

Intermediate 6

1-Phenylbicyclo[2.2.2]octane-4-carbaldehyde

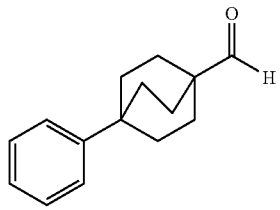

To an ice water cooled solution of N-methoxy-N-methyl-1-phenylbicyclo[2.2.2]octane-4-carboxamide (Intermediate 5; 8.49 g, 31.05 mmol) in anhydrous THF (100 mL) under nitrogen was added lithium aluminium hydride (1M solution in THF, 62 mL) dropwise and the reaction mixture was allowed to stir at 0° C. for 1 hr. Water (25 mL) was added cautiously followed by EtOAc (~100 mL) and the mixture was filtered through a pad of celite washing with EtOAc (50 mL). The filtrate was washed with brine (150 mL), the organic phase separated, dried (MgSO$_4$) and concentrated to leave the title compound as a colourless oil which formed a solid on standing (6.92 g, 32.28 mmol, 100%); $^1$H NMR (CDCl$_3$) δ 1.72-1.83 (6H, m), 1.87-1.94 (6H, m), 7.17-7.22 (1H, m), 7.31-7.33 (4H, m), 9.53 (1H, s); GC-MS EI m/e M$^+$ 214.

Intermediate 7

4-[2-Methoxyethenyl]-1-phenyl-bicyclo[2.2.2]octane

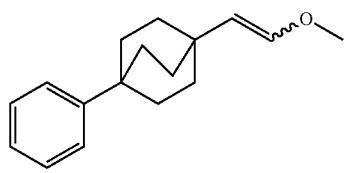

To an ice water cooled stirred suspension of (methoxymethyl)triphenylphosphonium chloride (17 g, 49.57 mmol) in anhydrous THF (100 mL) under nitrogen was added lithium bis(trimethylsilyl)amide (1M solution in THF; 50 mL, 50 mmol), and the reaction mixture was allowed to stir at 0° C. for 30 mins. 1-Phenylbicyclo[2.2.2]octane-4-carbaldehyde (Intermediate 6; 10.52 g, 49.08 mmol) in THF (20 mL) was added dropwise and the reaction mixture was allowed to stir at 0° C. for one hour and then at ambient temperature overnight. Water (100 mL) was added and the reaction mixture was partitioned between EtOAc (200 mL) and brine (100 mL), the organic phase was washed with an additional 100 mL of brine then separated, dried (MgSO$_4$) and concentrated to leave a pale yellow gum. The residue was purified on a 330 g Presearch silica cartridge, loading in isohexane/DCM and eluting 0-20% EtOAc-isohexane to provide the title compound as a pale yellow oil (12.6 g, 50.19 mmol, 100%) as a 1:2 mixture of E:Z isomers; E isomer $^1$H NMR (CDCl$_3$) δ 1.60-1.65 (2H, m), 1.82-1.88 (10H, m), 3.49 (3H, s), 4.74 (1H, d), 6.18 (1H, d), 7.12-7.18 (1H, m), 7.25-7.34 (4H, m); Z isomer: $^1$H NMR (CDCl$_3$) δ 1.60-1.65 (2H, m), 1.82-1.88 (10H, m), 3.54 (3H, s), 4.09 (1H, d), 5.71 (1H, d), 7.12-7.18 (1H, m), 7.25-7.34 (4H, m); MS (same for both individual isomers): GC-MS EI+ m/e 242 (M$^+$).

Intermediate 8

Methyl 2-(1-phenyl-4-bicyclo[2.2.2]octyl)acetate

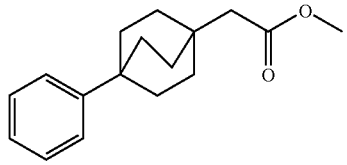

To a stirred solution of 4-[2-methoxyethenyl]-1-phenylbicyclo[2.2.2]octane (Intermediate 7; 12.6 g, 51.99 mmol) in DCM (200 mL) was added pyridinium chlorochromate (33.6 g, 155.97 mmol) in portions and the reaction mixture was allowed to stir at ambient temperature for 2 hrs. Further pyridinium chlorochromate (12 g, 55.99 mmol) was added and stirring was continued for a further 1 hr. The mixture was filtered and the filtrate was concentrated under reduced pressure, ether (200 mL) was added and the organic phase was washed with water (200 mL). Water (200 mL) and ether (2×200 mL) were added to the filtered solid and the mixture was filtered through a pad of celite. The organic extracts were combined, dried (MgSO$_4$) and concentrated to leave a brown gum. This was purified on a 330 g Crawford silica cartridge, loading the sample in DCM and eluting with 5-10-20% EtOAc-isohexane to provide the title compound as a cream solid (7.89 g, 30.53 mmol, 59%); $^1$H NMR (CDCl$_3$) δ 1.63-1.71 (6H, m), 1.83-1.93 (6H, m), 2.17 (2H, s), 3.67 (3H, s), 7.14-7.19 (1H, m), 7.29-7.32 (4H, m); GC-MS EI m/e M$^+$ 258.

Intermediate 9

Methyl {4-[4-(2-bromo-2-methylpropanoyl)phenyl]bicyclo[2.2.2]oct-1-yl}acetate

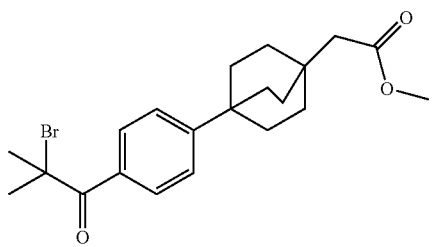

To an ice water cooled solution of methyl (4-phenylbicyclo[2.2.2]oct-1-yl)acetate (Intermediate 8; 3.88 g, 15.02 mmol) in DCM (150 mL) was added aluminium chloride (6.01 g, 45.05 mmol) followed by the dropwise addition of 2-bromoisobutyryl bromide (1.86 mL, 15.02 mmol). The reaction mixture was allowed to stir at ~0° C. for 30 mins then poured onto ice-water (20 mL). The organic phase was separated and the aqueous phase washed with DCM (2×150 mL), the organic washings combined, dried (MgSO$_4$) and concentrated to leave a yellow gum. This was purified on a 120 g Crawford silica cartridge, loading in DCM and eluting with 0-10%-20% isohexane-EtOAc to give the product as a white solid (5.18 g, 12.72 mmol, 85%). $^1$H NMR (CDCl$_3$) δ 1.64-1.69 (6H, m), 1.83-1.88 (6H, m), 2.03 (6H, s), 2.18 (2H, s), 3.66 (3H, s), 7.36 (2H, d), 8.10 (2H, d); Solid Probe MS m/e M$^+$ 407.

Intermediate 10

Methyl {4-[4-(4-amino-7,7-dimethyl-7H-pyrimido[4,5-b][1,4]oxazin-6-yl)phenyl]bicyclo[2.2.2]oct-1-yl}acetate Note: Intermediate 10 is the same compound as Intermediate 1.

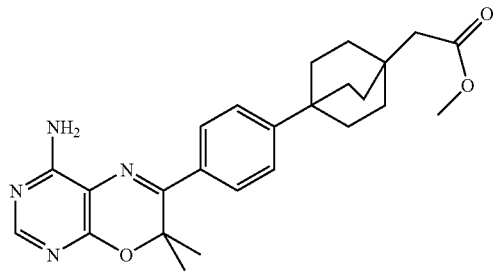

To a solution of 5,6-diaminopyrimidin-4-ol (280 mg, 2.2 mmol) in water (8 mL), absolute ethanol (25 mL) and 1M HCl (2.2 mL, 2.2 mmol) was added a solution of methyl {4-[4-(2-bromo-2-methylpropanoyl)phenyl]bicyclo[2.2.2]oct-1-yl}acetate (Intermediate 9; 877 mg, 2.15 mmol) in absolute EtOH (80 mL). The solution was heated to 100° C. overnight then allowed to cool to ambient temperature, evaporated to dryness, and the residue treated with 2M NaOH to adjust the pH to 10. The resulting suspension was filtered to provide a yellow solid which was purified on a 12 g presearch silica cartridge dry loading on silica (2 g) and eluting with 0-2.5-5% MeOH-DCM to provide the title compound as a white solid (601 mg, 1.38 mmol, 64%) $^1$H NMR δ 1.59-1.63 (12H, m), 1.79-1.83 (6H, m), 2.16 (2H, s), 3.59 (3H, s), 6.91 (2H, s), 7.39 (2H, d), 7.64 (2H, d), 7.95 (1H, s); MS m/e MH$^+$ 435.

Example 2

{3-[4-(4-Amino-7,7-dimethyl-7H-pyrimido[4,5-b][1,4]oxazin-6-yl)phenyl]-1-adamantyl}acetic acid

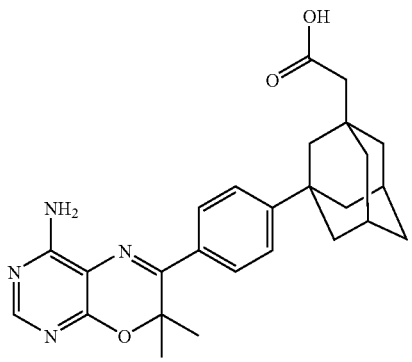

Prepared according to the procedure described for example 1 (first preparation) using methyl {3-[4-(4-amino-7,7-dimethyl-7H-pyrimido[4,5-b][1,4]oxazin-6-yl)phenyl]-1-adamantyl}acetate (Intermediate 13) to provide the title compound in 58% yield; $^1$H NMR δ 1.67 (s, 6H), 1.69 (s, 6H), 1.78 (s, 2H), 1.88 (s, 4H), 2.12 (s, 2H), 2.20 (s, 2H), 6.96 (s, 2H), 7.47 (d, 2H), 7.73 (d, 2H), 8.01 (s, 1H); MS m/e MH$^+$ 447.

Intermediate 11

Methyl (3-phenyl-1-adamantyl)acetate

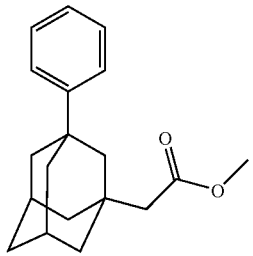

To an ice-water cooled solution of 3-phenyladamantane-1-carboxylic acid (735 mg, 2.87 mmol) in DCM (50 mL) was added DMF (2-3 drops) followed by oxalyl chloride (0.25 mL). The reaction mixture was allowed to stir at 0° C. for 6 hrs, the solvent was evaporated under reduced pressure to leave crude acid chloride which was used directly. This was redissolved in a 1:1 mixture of MeCN and THF (10 mL) and added dropwise to an ice water cooled solution of trimethylsilyldiazomethane (2M; 2.0 mL) and triethylamine (0.50 mL, 3.58 mmol) in a 1:1 mixture of MeCN and THF (20 mL). The resulting yellow reaction mixture was allowed to warm to ambient temperature overnight. The solvent was removed under reduced pressure and the residue redissolved in EtOAc (50 mL) and washed with water (50 mL), NaHCO$_3$ (50 mL) and brine (50 mL). The organic phase was dried (MgSO$_4$), concentrated to leave a red brown gum, (344 mg). This was purified on a 12 g Crawford silica cartridge, loading in DCM and eluting with 0-20% EtOAc. Isolated 2-diazo-1-(3-phenyl-1-adamantyl)ethanone as a yellow gum (699 mg, 2.49 mmol, 87%). $^1$H NMR (CDCl$_3$) δ 1.74 (s, 2H), 1.83 (s, 4H), 1.91-1.94 (m, 6H), 2.27 (s, 2H), 5.43 (s, 1H), 7.18-7.22 (m, 2H), 7.31-7.38 (m, 4H); GC-MS CI m/e MH$^+$ 281.

The diazoketone (699 mg, 2.49 mmol) was dissolved in methanol (25 mL) and placed in an ultrasound bath. A solution of silver benzoate (114 mg, 0.498 mmol) in triethylamine (1.4 mL, 9.96 mmol, 4 eq) was added dropwise and the mixture was sonicated for 1 hr. The methanol was removed by evaporation and the residue dissolved in EtOAc (50 mL) and washed with NaHCO$_3$ (40 mL), citric acid (2M, 40 mL), brine (40 mL), dried (MgSO$_4$) and concentrated to leave a yellow oil. This was purified on a 12 g silica cartridge loading in DCM and eluting with 10-20% EtOAc-isohexane to provide the title compound as a pale yellow gum (421 mg, 1.48 mmol; 59% from the diazoketone). $^1$H NMR (CDCl$_3$) δ 1.64-1.70 (m, 5H), 1.76 (s, 2H), 1.86-1.96 (m, 5H), 2.17 (s, 2H), 2.18-2.19 (m, 2H), 3.65 (s, 3H), 7.15-7.20 (m, 1H), 7.29-7.37 (m, 4H); GC-MS EI m/e M$^+$ 284.

Intermediate 12

Methyl {3-[4-(2-bromo-2-methylpropanoyl)phenyl]-1-adamantyl}acetate

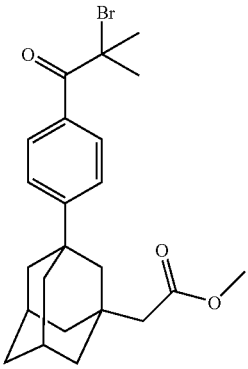

Prepared according to the procedure described for Intermediate 9 using methyl (3-phenyl-1-adamantyl)acetate, the title compound being isolated in 35% yield: $^1$H NMR (CDCl$_3$) δ 1.66 (d, 4H), 1.71 (s, 2H), 1.77 (s, 2H), 1.87 (s, 4H), 2.04 (s, 6H), 2.18 (s, 2H), 2.20-2.22 (m, 2H), 3.65 (s, 3H), 7.41 (d, 2H), 8.12 (d, 2H); GC-MS CI m/e MH$^+$ 433.

Intermediate 13

Methyl {3-[4-(4-amino-7,7-dimethyl-7H-pyrimido[4,5-b][1,4]oxazin-6-yl)phenyl]-1-adamantyl}acetate

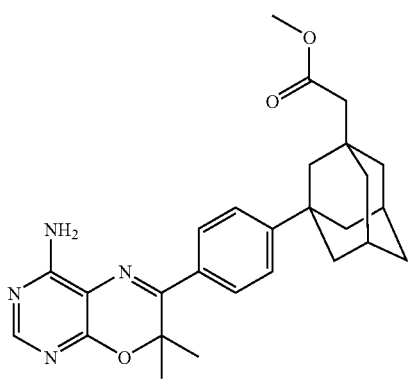

Prepared according to the procedure described for Intermediate 1 (iv), using methyl {3-[4-(2-bromo-2-methylpropanoyl)phenyl]-1-adamantyl}acetate (Intermediate 12), isolating the title compound in 44% yield: $^1$H NMR δ 1.62 (s, 6H), 1.65-1.69 (m, 6H), 1.71 (s, 2H), 1.83 (s, 4H), 2.15 (s, 2H), 2.17 (s, 2H), 3.58 (s, 3H), 6.92 (s, 2H), 7.42 (d, 2H), 7.68 (d, 2H), 7.96 (s, 1H); MS m/e MH$^+$ 461.

Example 3

3-[4-(4-Amino-7,7-dimethyl-7H-pyrimido[4,5-b][1,4]oxazin-6-yl)phenyl]adamantane-1-carboxylic acid

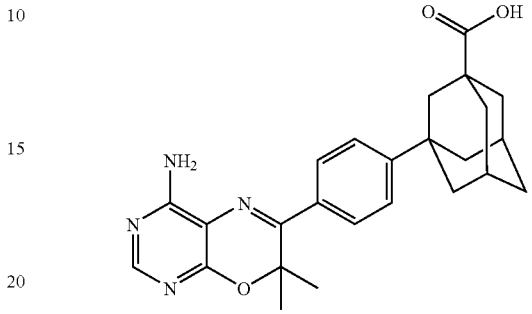

Prepared according to the procedure described for Example 1 (first preparation) using methyl 3-[4-(4-amino-7,7-dimethyl-7H-pyrimido[4,5-b][1,4]oxazin-6-yl)phenyl] adamantane-1-carboxylate (Intermediate 15), providing the title compound in 25% yield; $^1$H NMR δ 1.62 (s, 6H), 1.70-1.72 (m, 2H), 1.83-1.88 (m, 7H), 2.16-2.19 (m, 2H), 6.92 (s, 2H), 7.45 (d, 2H), 7.68 (d, 2H), 7.96 (s, 1H); MS m/e MH$^+$ 433.

Intermediate 14

Methyl 3-[4-(2-bromo-2-methylpropanoyl)phenyl] adamantane-1-carboxylate

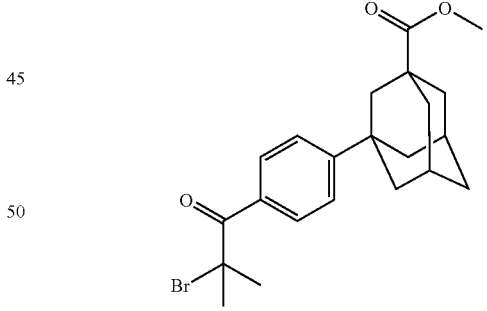

Prepared according to the procedure described for Intermediate 1 (iii) using methyl 3-phenyladamantane-1-carboxylate (CAS number 27011-58-1, Stepanov, F. N.; Dovgan, N. L. Kiev. Politekh. Inst., Kiev, USSR. Zhurnal Organicheskoi Khimii (1970), 6(8), 1623-7. or Danilenko, G. I.; Krayushkin, M. M.; Sevost'yanova, V. V. Inst. Org. Khim. im. Zelinskogo, Moscow, USSR. Izvestiya Akademii Nauk SSSR, Seriya Khimicheskaya (1970), (2), 444-5). The title compound was isolated in 89% yield: $^1$H NMR (CDCl$_3$) δ 1.91-1.93 (m, 8H), 2.04 (s, 6H), 2.23-2.27 (m, 6H), 4.52 (s, 3H), 7.42 (d, 2H), 8.13 (d, 2H); GC-MS CI m/e MH$^+$ 421.

Intermediate 15

Methyl 3-[4-(4-amino-7,7-dimethyl-7H-pyrimido[4,5-b][1,4]oxazin-6-yl)phenyl]adamantane-1-carboxylate

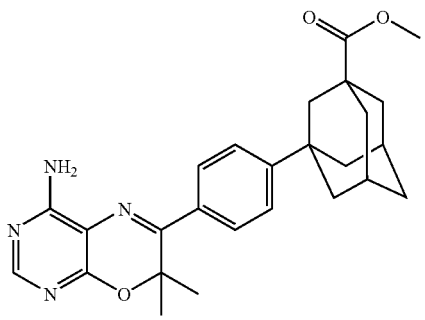

Prepared according to the procedure described for Intermediate 1(iv) using methyl 3-[4-(2-bromo-2-methylpropanoyl)phenyl]adamantane-1-carboxylate, the title compound being isolated in 44% yield and used directly in the next stage without full characterisation; MS m/e MH$^+$ 447.

Example 4

2-{4-[4-(4-Amino-7,7-dimethyl-7H-pyrimido[4,5-b][1,4]oxazin-6-yl)phenyl]bicyclo[2.2.2]oct-1-yl}propanoic acid

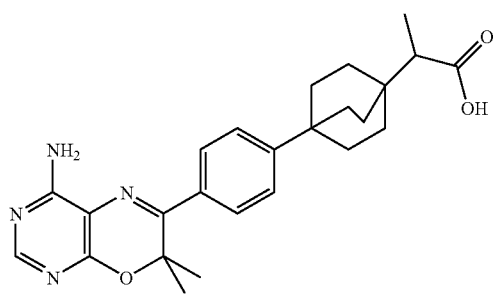

A mixture of methyl 2-{4-[4-(4-amino-7,7-dimethyl-7H-pyrimido[4,5-b][1,4]oxazin-6-yl)phenyl]bicyclo[2.2.2]oct-1-yl}propanoate (Intermediate 18; 220 mg, 0.49 mmol) and potassium trimethylsilanolate (315 mg, 2.45 mmol) in THF (5 mL) was heated in a microwave for 35 mins at 100° C. and was then stirred at ambient temperature for 2 days. The solvent was removed under reduced pressure and the residue partitioned between 2M HCl (20 mL) and EtOAc (50 mL) and the aqueous phase was further extracted with EtOAc (50 mL). The organic extracts were combined, dried (MgSO$_4$) and concentrated to leave a gum. This was dissolved in DMSO/MeCN/H$_2$O (7:2:1) and separated by reverse phase chromatography eluting 5-95% water-acetonitrile 0.2% TFA, providing the title compound (45 mg, 0.104 mmol, 21%) as a white solid; $^1$H NMR δ 1.01 (d, 3H), 1.49-1.55 (m, 3H), 1.62 (s, 6H), 1.64-1.69 (m, 3H), 1.78-1.81 (m, 6H), 2.12 (q, 1H), 7.05 (s, 1H), 7.40 (d, 2H), 7.65 (d, 2H), 7.99 (s, 1H); MS m/e MH$^+$ 435.

Intermediate 16

Methyl 2-(4-phenylbicyclo[2.2.2]oct-1-yl)propanoate

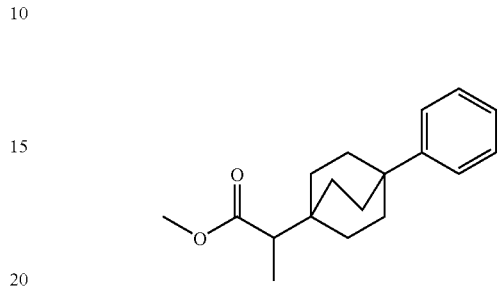

To a solution of diisopropylamine (0.9 mL, 6.39 mmol) in anhydrous THF (10 mL) cooled to −78° C. (CO$_2$/acetone) was added nBuLi (2M solution in cyclohexane; 3.2 mL, 6.4 mmol) and the reaction mixture was allowed to stir at −78° C. for 5 mins. Methyl (4-phenylbicyclo[2.2.2]oct-1-yl)acetate (Intermediate 1(ii); 1.5 g, 5.81 mmol) in anhydrous THF (2 mL) was added and the mixture immediately became dark brown/black. It was allowed to stir for ~30 mins at −78° C. then methyl iodide (0.4 mL, 6.39 mmol) was added and the reaction mixture was allowed to warm to ambient temperature over 4 hrs. Saturated aqueous ammonium chloride solution (50 mL) was added and the mixture extracted into EtOAc (2×150 mL), the organic extracts were combined, dried (MgSO$_4$) and concentrated to leave crude product which was an inseparable mixture of the title compound and starting material which was taken directly through to the next stage without further characterisation.

Intermediate 17

Methyl {4-[4-(2-bromo-2-methylpropanoyl)phenyl]bicyclo[2.2.2]oct-1-yl}acetate

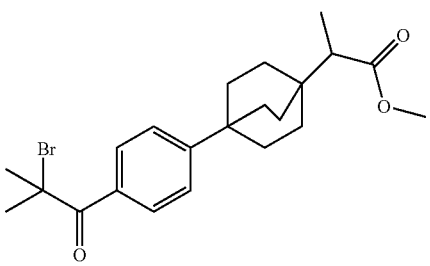

To an ice water cooled solution of crude methyl (4-phenylbicyclo[2.2.2]oct-1-yl)acetate (Intermediate 16; 961 mg, 3.53 mmol) in DCM (10 mL) was added aluminium chloride (1.4 g, 10.58 mmol) followed by the dropwise addition of 2-bromoisobutyryl bromide (0.45 mL, 3.53 mmol). The reaction mixture was allowed to stir at ~0° C. for ~40 mins, it was then poured onto ice-water (~100 mL). The organic phase was separated and the aqueous phase washed with DCM (3×50 mL), the organic washings were combined, dried (MgSO₄) and concentrated to leave a yellow gum. This was purified on a 120 g silicyle silica cartridge, loading in DCM and eluting with 0-10%-20% isohexane-EtOAc, the product eluting at 10% EtOAc. The mixed fractions were combined and recolumned on a 120 g silica cartridge as described above; to yield the title compound as a white solid, (705 mg 1.67 mmol, 47%). $^1$H NMR (CDCl₃) δ 1.09 (d, 3H), 1.50-1.57 (m, 3H), 1.67-1.74 (m, 3H), 1.82-1.86 (m, 6H), 2.03 (s, 6H), 2.27 (q, 1H), 3.67 (s, 3H), 7.37 (d, 2H), 8.11 (d, 2H); GC-MS CI m/e MH⁺ 421.

Intermediate 18

Methyl 2-{4-[4-(4-amino-7,7-dimethyl-7H-pyrimido[4,5-b][1,4]oxazin-6-yl)phenyl]bicyclo[2.2.2]oct-1-yl}ropanoate

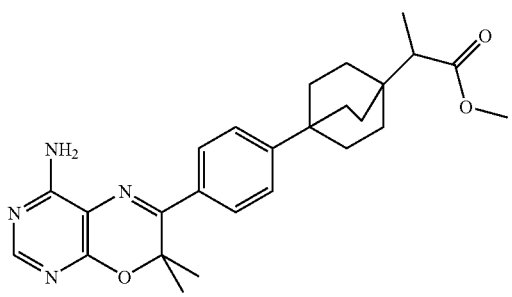

4,5-Diamino-6-hydroxypyrimidine hemisulfate (~5 g) was converted into the free base by suspending it in a mixture of DMF (600 mL) and MeCN (100 mL), adding polymer supported carbonate and allowing the mixture to stand at ambient temperature for 24 hours (stirring occasionally). The suspension was filtered and the filtrate concentrated to leave a yellow-orange solid (1.76 g). The free base (233 mg, 1.84 mmol) followed by 1M HCl (2.0 mL) was added to a solution of methyl {4-[4-(2-bromo-2-methylpropanoyl)phenyl]bicyclo[2.2.2]oct-1-yl}acetate (Intermediate 17; 705 mg, 1.67 mmol) in abs EtOH (20 mL). The suspension was heated under gentle reflux overnight. The mixture was allowed to cool to ambient temperature and then evaporated to dryness and the residue treated with 2M NaOH to adjust the pH to ~10. The suspension was filtered to provide a yellow solid and the filtrate was extracted into EtOAc (2×100 mL), the organic extracts separated, dried (MgSO₄) and concentrated to leave a pale yellow gum. The combined products were purified on a 12 g Crawford silicycle cartridge, dry loading the sample on deactivated silica and eluting 0-5% DCM-MeOH using an Isco companion, to provide the title compound (220 mg, 0.491 mmol, 29%) as a cream solid; $^1$H NMR δ 1.02 (d, 3H), 1.44-1.52 (m, 3H), 1.61-1.67 (m, 9H), 1.77-1.79 (m, 6H), 2.24 (q, 1H), 3.60 (s, 3H), 6.89 (s, 2H), 7.39 (d, 2H), 7.64 (d, 2H), 7.95 (s, 1H); MS m/e MH⁺ 449.

Example 5

{5-[4-(4-Amino-7,7-dimethyl-7H-pyrimido[4,5-b][1,4]oxazin-6-yl)phenyl]bicyclo[3.2.2]non-1-yl}acetic acid

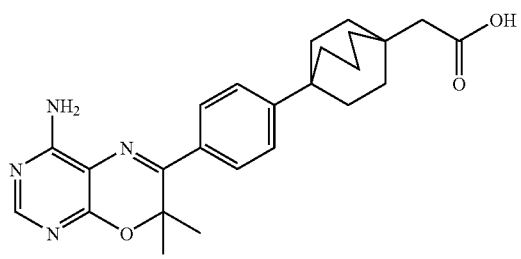

To a solution of methyl {5-[4-(4-amino-7,7-dimethyl-7H-pyrimido[4,5-b][1,4]oxazin-6-yl)phenyl]bicyclo[3.2.2]non-1-yl}acetate (Intermediate 25; 55 mg, 0.12 mmol) in MeOH (5 mL) was added 2M NaOH (0.3 mL) and the reaction mixture was allowed to stir at ambient temperature overnight, then at 50° C. for 8 hrs and ambient temperature overnight. The solvent was removed under reduced pressure and the residue was acidified to pH 2 with 2M HCl, the filtrate extracted into EtOAc (2×50 mL), the organic extracts combined, dried (MgSO₄) and concentrated to leave a yellow gum. The product was purified by reverse phase preparative HPLC, loading the sample in DMSO/MeCN/H₂O (7:2:1) and eluting with 5-95 water-MeCN with 0.2% TFA in each phase, to provide the title compound (31 mg, 0.0714 mmol, 59%) as a pale yellow solid, $^1$H NMR δ 1.34-1.56 (14H, m), 1.63 (6H, s), 1.95 (2H, s), 7.15 (2H, d), 7.63-7.66 (2H, m), 8.02 (1H, s); MS m/e MH⁺ 435

Intermediate 19

Bicyclo[3.2.2]nonane-1,5-dicarboxylic acid monomethyl ester

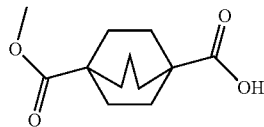

To a stirred solution of dimethyl bicyclo[3.2.2]nonane-1,5-dicarboxylate (2.02 g, 8.41 mmol), in methanol (20 mL) and water (4 mL) was added barium hydroxide octahydrate (1.33 g, 4.20 mmol). The reaction mixture was stirred vigorously at ambient temperature overnight. The reaction mixture was stirred vigorously at ambient temperature overnight. The reaction mixture was diluted with water (20 mL) and washed with isohexane (2×100 mL), then the aqueous phase was acidified with 2M HCl to pH 2 and extracted into EtOAc (2×100 mL). The organic extracts were combined, dried (MgSO₄) and concentrated to leave the title compound (931 mg, 4.11 mmol, 49%) as a clear colourless gum which slowly Intermediate 20

Methyl 5-bromobicyclo[3.2.2]nonane-1-carboxylate

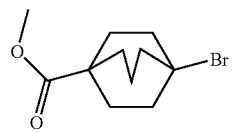

To a stirred suspension (Intermediate 19; 3.43 g, 15.16 mmol) in acetone (25 mL) was added 1M NaOH (16 mL) and the resulting clear pale yellow solution was allowed to stir at ambient temperature for 10 mins. A solution of silver nitrate (2.73 g, 16.07 mmol) in water (4 mL) was added dropwise and an immediate thick brown suspension formed which was allowed to stir at ambient temperature for a further 60 mins. The suspension was filtered, washed with water (100 mL), acetone (100 mL) and ether (100 mL). It was dried in under vacuum overnight at 45° C. to leave a brown solid (4.42 g).

To a suspension of this silver salt (4.24 g, 12.73 mmol) in 40-60 petroleum ether (50 mL) under nitrogen was added bromine (0.65 mL, 12.73 mmol) dropwise. The resulting orange suspension was stirred at ambient temperature for 30 mins then at 60° C. for 40 mins. The reaction mixture was allowed to cool to ambient temperature, the suspension was filtered and the solid was washed with ether (3×100 mL) then 1M sodium carbonate (3×150 mL). The organic phase was separated, washed with brine (100 mL), dried (MgSO$_4$) and concentrated to leave the title compound (1.22 g, 4.67 mmol, 37%) as a pale yellow oil; $^1$H NMR (CDCl$_3$) δ 1.69-1.75 (m, 2H), 1.83-2.00 (m, 6H), 2.43-2.50 (m, 6H), 3.65 (s, 3H); GC-MS CI m/e MH$^+$ 261.

Intermediate 21

5-Phenylbicyclo[3.2.2]nonane-1-carboxylic acid

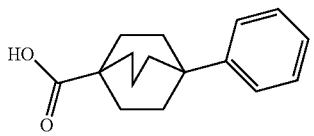

A solution of methyl 5-bromobicyclo[3.2.2]nonane-1-carboxylate (Intermediate 20; 1.22 g, 4.67 mmol) in anhydrous benzene (5 mL) was added dropwise to an ice water cooled suspension of aluminium chloride (2.3 g, 17.28 mmol) in benzene (5 mL) under nitrogen. The resulting reaction mixture was allowed to stir in the ice bath for ~30 mins, then removed from the cooling bath and allowed warm to and stir at ambient temperature overnight. Then mixture was heated to 60° C. for 4 hrs and then was allowed to cool to ambient temperature and cautiously poured onto a mixture of ice (30 g) and concentrated HCl (5 mL). The mixture was extracted into ether (4×100 mL), the extracts combined, washed with brine (50 mL), and dried (MgSO$_4$) to leave an orange-brown gum (821 mg). The crude material was redissolved in a mixture of MeOH (20 mL) and 2M NaOH (8 mL) and allowed to stir at ambient temperature overnight. The solvent was removed and the residue partitioned between NaOH and ether, the aqueous phase was then acidified and extracted into EtOAc. The organic extracts were dried and concentrated to give the title compound (534 mg, 2.18 mmol, 47%) as a brown gum; $^1$H NMR δ 1.34-1.38 (m, 6H), 1.61-1.65 (m, 6H), 2.40 (s, 2H), 7.07 (d, 2H), 7.16-7.20 (m, 1H), 7.24-7.28 (m, 2H), 11.87 (s, 1H); GC-MS EI m/e M 244.

Intermediate 22

2-Diazo-1-(4-phenylbicyclo[3.2.2]non-1-yl)ethanone

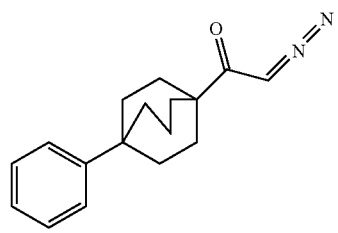

To a solution of 5-phenylbicyclo[3.2.2]nonane-1-carboxylic acid (Intermediate 21; 534 mg, 2.19 mmol) in DCM (10 mL) was added DMF (2 drops) followed by oxalyl chloride (0.3 mL, 3.28 mmol). The reaction mixture was allowed to stir at ambient temperature overnight, the solvent was evaporated under reduced pressure to leave crude acid chloride which was used directly.

This was redissolved in a 1:1 solution of MeCN and THF (10 mL) and added dropwise to an ice water cooled solution of trmethylsilyldiazomethane (2M; 1.5 mL, 3.0 mmol) and triethylamine (0.4 mL, 2.73 mmol) in a 1:1 mixture of MeCN and THF (20 mL). The reaction mixture was allowed to stir at 0° C. for 1 hr and then for 5 hrs and ambient temperature and allowed to stand over the weekend. The solvent was removed under reduced pressure and the residue redissolved in EtOAc (250 mL) and washed with water (100 mL), saturated aqueous NaHCO$_3$ solution (150 mL) and brine (150 mL). The organic phase was dried (MgSO$_4$), and concentrated to leave a brown gum. This was purified on a 40 g Crawford silicycle cartridge loading in DCM and eluting with 0-10% EtOAc-isohexane, to provide the title compound (252 mg, 0.940 mmol, 43%) as an orange gum; $^1$H NMR (CDCl$_3$) δ 1.24-1.29 (1H, m), 1.43-1.47 (6H, m), 1.61-1.67 (6H, m), 5.28 (1H, s), 7.05-7.24 (5H, m).

Intermediate 23

Methyl (5-phenylbicyclo[3.2.2]non-1-yl)acetate

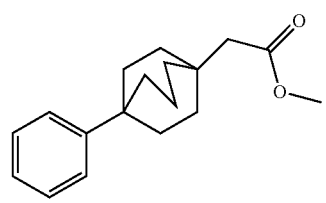

2-Diazo-1-(4-phenylbicyclo[3.2.2]non-1-yl)ethanone (Intermediate 22; 252 mg, 0.94 mmol) was dissolved in methanol (10 mL), a solution of silver benzoate (44 mg, 0.19 mmol) in triethylamine (0.52 mL, 3.76 mmol) was added dropwise and the mixture sonicated in an ultrasound bath for 1 hr. The methanol was removed by evaporation and the residue dissolved in EtOAc (20 mL), filtered through a pad of celite and washed with NaHCO$_3$ (10 mL), aqueous citric acid (2M, 10 mL), brine (10 mL) then dried (MgSO$_4$) and concentrated to leave a brown gum, 229 mg which was taken directly through to the next stage without further characterisation.

Intermediate 24

Methyl {5-[4-(2-bromo-2-methylpropanoyl)phenyl] bicyclo[3.2.2]non-1-yl}acetate

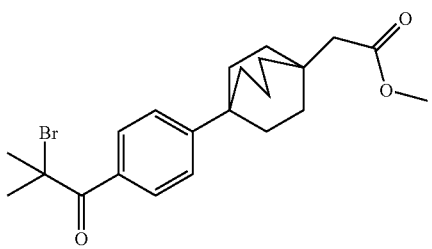

To an ice water cooled solution of methyl (5-phenylbicyclo [3.2.2]non-1-yl)acetate (Intermediate 23; 229 mg, 0.79 mmol) in DCM (10 mL) was added aluminium chloride (318 mg, 2.38 mmol) followed by the dropwise addition of 2-bromoisobutyryl bromide (0.10 mL, 0.79 mmol). The reaction mixture was allowed to stir at 0° C. for 40 mins then poured onto ice-water (100 mL). The organic phase was separated and the aqueous phase washed with DCM (3×50 mL), the organic washings were combined, dried (MgSO$_4$) and concentrated to leave a yellow gum. This was purified on a 12 g Crawford silicyle cartridge, loading in DCM and eluting with 0-10%-20% isohexane-EtOAc to provide the title compound (85 mg, 0.202 mmol, 26%) as a pale yellow gum; $^1$H NMR (CDCl$_3$) δ 1.09 (d, 3H), 1.50-1.57 (m, 3H), 1.67-1.74 (m, 3H), 1.82-1.86 (m, 6H), 2.03 (s, 6H), 2.27 (q, 1H), 3.67 (s, 3H), 7.37 (d, 2H), 8.11 (d, 2H); GC-MS CI m/e MH$^+$ 421.

Intermediate 25

Methyl {5-[4-(4-amino-7,7-dimethyl-7H-pyrimido [4,5-b][1,4]oxazin-6-yl)phenyl]bicyclo[3.2.2]non-1-yl}acetate

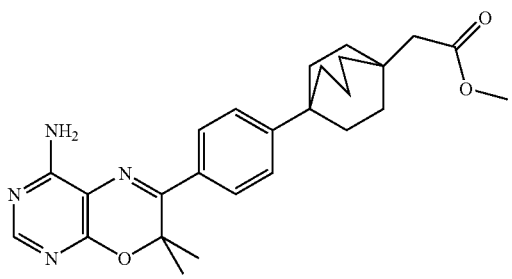

4,5-Diamino-6-hydroxypyrimidine hemisulfate (~5 g) was converted into the free base by suspending it in a mixture of DMF (600 mL) and MeCN (100 mL), adding polymer supported carbonate and allowing the mixture to stand at ambient temperature for 24 hours (stirring occasionally). The suspension was filtered and the filtrate concentrated to leave a yellow-orange solid (1.76 g).

To a solution of methyl {5-[4-(2-bromo-2-methylpropanoyl)phenyl]bicyclo[3.2.2]non-1-yl}acetate (Intermediate 24; 80 mg, 0.19 mmol) in absolute EtOH (20 mL) was added 5,6-diaminopyrimidin-4-ol (30 mg, 0.21 mmol) followed by 1M HCl (0.21 mL). The suspension was heated under gentle reflux (80° C.) overnight then allowed to cool, the solvent removed and the residue treated with 2M NaOH (2 mL). The aqueous phase was extracted into EtOAc (3×50mL), the organic extracts were combined, dried (MgSO$_4$) and concentrated to leave a pale yellow gum. This was purified on a 12 g Crawford silicycle cartridge, loading in DCM and eluting with 0-5-10% MeOH-DCM, giving the title compound as a pale yellow gum (55 mg, 0.123 mmol, 65%); $^1$H NMR (CDCl$_3$) 1.41-1.61 (14H, m), 1.71 (6H, s), 2.07 (2H, s), 3.61 (3H, s), 7.11 (2H, d), 7.51 (2H, d), 8.14 (1H, s); MS m/e MH$^+$ 449.

Example 6

4-[4-(4-Amino-7,7-dimethyl-7H-pyrimido[4,5-b][1, 4]oxazin-6-yl)phenyl]bicyclo[2.2.2]octane-1-carboxylic acid

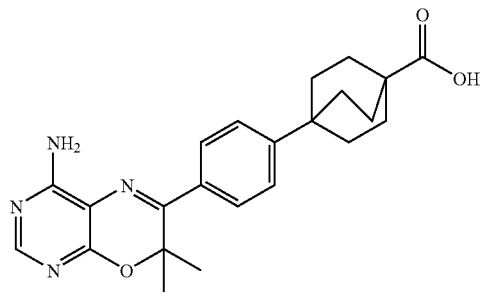

To a solution of methyl 4-[4-(4-amino-7,7-dimethyl-7H-pyrimido[4,5-b][1,4]oxazin-6-yl)phenyl]bicyclo[2.2.2]octane-1-carboxylate (Intermediate 27; 140 mg, 0.33 mmol) in MeOH (10 mL) was added 2M NaOH (0.82 mL, 1.66 mmol). The reaction mixture was allowed to stir at ambient temperature overnight and then after the addition of EtOH (~5 mL) and 1M NaOH (2 mL) the reaction mixture was heated to 50° C. for 5.5 hrs. The organic solvent was removed by evaporation under reduced pressure and the residue was acidified to pH 2 with 2M HCl. EtOAc was added and the suspension was filtered and dried to provide the title compound (97 mg, 2.39 mmol, 72%); $^1$H NMR δ 1.60 (s, 6H), 1.82 (s, 12H), 6.97 (s, 1H), 7.40 (d, 2H), 7.65 (d, 2H), 7.95 (s, 1H), NH$_2$ not seen; MS m/e MH$^+$ 407.

Intermediate 26

Methyl 4-[4-(2-bromo-2-methylpropanoyl)phenyl]bicyclo[2.2.2]octane-1-carboxylate

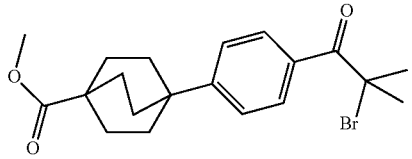

To an ice/IPA cooled solution of methyl 4-phenylbicyclo[2.2.2]octane-1-carboxylate (obtained using the procedure described by N. B Chapman, S. Sotheeswaran and K. J. Toyne *J. Org. Chem.*, 1970, 35, (4), 917) (412 mg, 1.69 mmol) in DCM (20 mL) was added aluminum chloride (680 mg, 5.06 mmol) followed by the dropwise addition of 2-bromoisobutyryl bromide (0.21 mL, 1.69 mmol). The reaction mixture was allowed to stir at 0° C. for 30 mins and then poured onto ice-water (~50 mL). The aqueous mixture was extracted into DCM (3×100 mL), the organic extracts were combined, washed with brine (100 mL), dried (MgSO$_4$) and concentrated to leave crude product. This was purified on a 12 g Redisep silica cartridge, loading sample in DCM and eluting with ether/isohexane (1:9) to provide the title compound as an orange solid, 507 mg (1.29 mmol, 76%); $^1$H NMR (CDCl$_3$) δ 1.87-1.95 (m, 12H), 2.04 (s, 6H), 3.68 (s, 3H), 7.38 (d, 2H), 8.11 (d, 2H); GC-MS CI m/e MH$^+$ 407.

Intermediate 27

Methyl 4-[4-(4-amino-7,7-dimethyl-7H-pyrimido[4,5-b][1,4]oxazin-6-yl)phenyl]bicyclo[2.2.2]octane-1-carboxylate

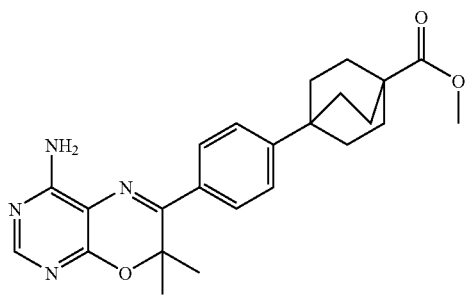

To a solution of methyl 4-[4-(2-bromo-2-methylpropanoyl)phenyl]bicyclo[2.2.2]octane-1-carboxylate (Intermediate 26; 507 mg, 1.29 mmol) in abs EtOH (10 mL) was added 5,6-diaminopyrimidin-4-ol (179 mg, 1.42 mmol) followed by 1M HCl (1.4 mL). The suspension was heated under reflux overnight, the reaction mixture was allowed to cool to ambient temperature and then evaporated to dryness. The residue treated with 2M potassium carbonate solution to adjust the pH to 10 and then the mixture was extracted into EtOAc (4×50 mL). The organic extracts were combined, dried (MgSO$_4$) and concentrated to leave the title compound as a yellow gum which was purified on a 12 g Redisep silica cartridge, dry loading the sample on Merck silica (deactivated, ~1 g) and eluting with DCM-MeOH 0-2%-5% to provide the title compound 150 mg (0.357 mmol, 27%); $^1$H NMR δ 1.61 (s, 6H), 1.84 (s, 12H), 3.61 (s, 3H), 6.98 (s, 2H), 7.41 (d, 2H), 7.66 (d, 2H), 7.95 (s, 1H); MS m/e MH$^+$ 421.

Example 7

Homologation via Alcohol, Tosylate and Nitrile
(4-Phenylbicyclo[2.2.2]oct-1-yl)methanol A solution of ethyl 4-phenylbicyclo[2.2.2]octane-1-carboxylate (207 g, 801 mmol) in THF (850 mL) was added to a stirred solution of lithium aluminium hydride (20 g, 527 mmol) in THF (1.25 L) under nitrogen, maintaining a temperature of 20-25° C. with an ice/water bath. The reaction mixture was stirred for 3 h, allowed to stand overnight, then quenched by addition to a mixture of water (900 mL) and ice (300 g). The mixture was acidified to pH 1-2 with concentrated hydrochloric acid then extracted with ethyl acetate (3×1 L). The combined organics were dried (MgSO$_4$) and evaporated down to give the title compound as a brown solid (176 g; ~100%). $^1$H NMR (CDCl$_3$) 1.35 (1H, brd s), 1.40-1.52 (6H, m), 1.71-1.85 (6H, m), 3.25 (2H, s), 7.05-7.13 (1H, m), 7.17-7.30 4H, m).

4-Phenylbicyclo[2.2.2]oct-1-ylmethyl toluene-4-sulfonate

Pyridine (4 mL), then a solution of toluene-4-sulfonyl chloride (7.4 g, 38.81 mmol) in dry DCM (30 mL), were added to a stirred solution of (4-phenylbicyclo[2.2.2]oct-1-yl)methanol (7.0 g, 32.36 mmol) in DCM (70 mL), maintaining 0-5° C. throughout. The reaction mixture was stirred at 0° C. overnight, refluxed for 2 h then cooled to 35° C. Further pyridine (2 mL) and a solution of toluene-4-sulfonyl chloride (3.9 g) in DCM (10 mL) were added and the mixture stirred at reflux for 2 h. As some starting material remained, a catalytic amount of 4-dimethylaminopyridine was added and the mixture stirred under reflux overnight. The mixture was cooled, diluted with DCM (200 mL) then washed with water (100 mL), hydrochloric acid (2M; 150 mL), water (50 mL), sat. aq. NaHCO$_3$ (100 mL), water (50 mL) and brine (50 mL). After drying (MgSO$_4$) the solution was concentrated to give crude product which was purified by silica column chromatography (silica 40-63 micron) eluting with hexane:ethyl acetate (19:1 to 4:1) to afford the title compound as a pale yellow solid (10.7 g, 89%).

$^1$H NMR (CDCl$_3$) 1.38-1.50 (6H, m), 1.68-1.79 (6H, m), 2.38 (3H, s), 3.62 (2H, s), 7.05-7.13 (1H, m), 7.15-7.25 (4H, m), 7.27 (2H, d), 7.73 (2H, d).

(4-Phenylbicyclo[2.2.2]oct-1-yl)acetonitrile

A stirred mixture of 4-phenylbicyclo[2.2.2]oct-1-ylmethyl toluene-4-sulfonate (2.5 g, 6.75 mmol) and sodium cyanide (0.5 g, 10.20 mmol) in DMSO (20 mL) was heated at 100° C. under nitrogen for 5 h. After cooling overnight the mixture was poured into water (100 mL) then extracted with DCM (2×100 mL) then methyl t-butyl ether (3×100 mL). The DCM and methyl t-butyl ether phases were separately combined, washed with water (50 mL) and dried (MgSO$_4$). The organic phases were then combined and the solvents evaporated to give the crude product which was purified by silica column chromatography (silica 40-63 micron) eluting with hexane: ethyl acetate 19:1 to give the title compound as a white solid (1.4 g; 93%).

$^1$H NMR (CDCl$_3$) 1.58-1.69 (6H, m), 1.79-1.89 (6H, m), 2.11 (2H, s), 7.07-7.13 (1H, m), 7.19-7.28 (4H, m).

(4-Phenylbicyclo[2.2.2]oct-1-yl)acetic acid

A solution of KOH (1.0 g, 17.52 mmol) in water (1.0 mL) was added to a suspension of (4-phenylbicyclo[2.2.2]oct-1-yl)acetonitrile (0.5 g) in ethylene glycol (10 mL) and the mixture stirred at 165° C. for 6 h, cooled, then poured in to water (100 mL). The mixture was acidified to pH 1 with conc. hydrochloric acid (~0.5 mL) then extracted with ethyl acetate (100 mL then 30 mL). The combined extracts were washed with water (2×50 mL), dried (MgSO$_4$) and concentrated down to give the title compound as a cream solid (0.5 g; 93%).
$^1$H NMR (CDCl$_3$) 1.57-1.69 (6H, m), 1.75-1.85 (6H, m), 2.12 (2H, s), 7.07-7.14 (1H, m), 7.19-7.28 (4H, m).

Methyl (4-phenylbicyclo[2.2.2]oct-1-yl)acetate

A freshly prepared solution of hydrogen chloride in methanol (~3 M; ~2 mL, ~6 mmol) was added to a solution of (4-Phenylbicyclo[2.2.2]oct-1-yl)acetic acid (0.3 g) in methanol (3 mL) under a calcium chloride guard tube and the mixture stirred for 4 h. The solvent was evaporated to leave the title compound as an off white solid (0.25 g; 78%).
$^1$H NMR (CDCl$_3$) 1.50-1.65 (6H, m), 1.71-1.83 (6H, m), 2.10 (2H, s), 3.58 (3H, s), 7.03-7.12 (1H, m), 7.17-7.28 (4H, m).

Example 8

Alternative Synthesis of Intermediate 4, Ethyl 4-phenylbicyclo[2.2.2]octane-1-carboxylate

Step 1: Ethyl 4-methoxy-2-oxo-bicyclo[2.2.2]octane-1-carboxylate

All equivalents and volumes are calculated from the starting material.

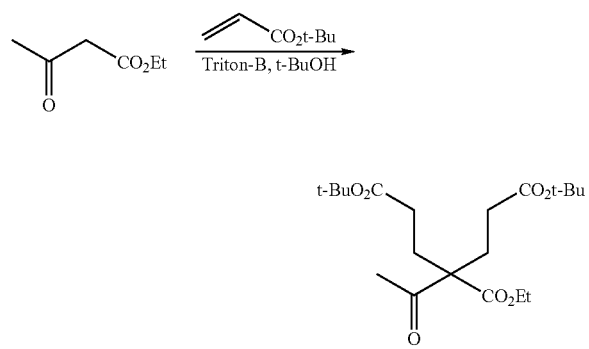

To a stirred solution of ethyl 3-oxobutanoate (1 eq) and Triton-B (40 wt % solution in water, 0.02 eq) in tert-butanol (1.2 v/w) under nitrogen was added tert-butyl acrylate (2.00 eq) drop-wise over 30 mins; a steady, persistent exotherm was noted that was controlled with ice/water cooling. Once the exotherm had abated, the solution was stirred at ambient temperature overnight.

The reaction mixture was partitioned between water (4.0 v/w) and MTBE (12.0 v/w). The separated aqueous phase was extracted further with MTBE (8.0 v/w) and the combined organic phases were dried over MgSO$_4$, filtered and concentrated in vacuo to afford the product as a pale yellow oil.

Step 2: 4-Acetyl-4-ethoxycarbonylheptanedioic acid

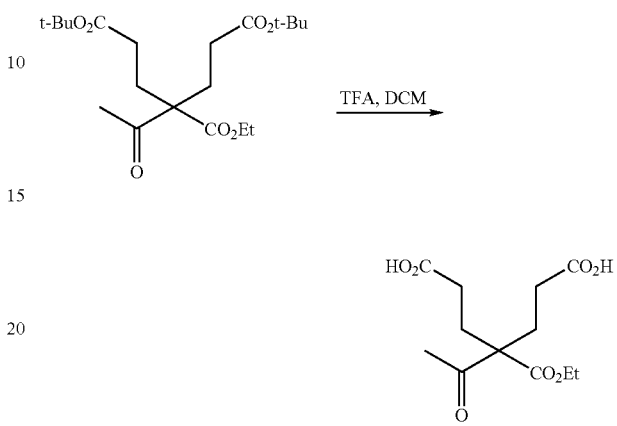

To a stirred solution of Step 1 product (1 eq) in DCM (2.6 v/w) at 0° C. under nitrogen was added a solution of TFA (2.6 v/w) in DCM (2.6 v/w) over 2 hrs, maintaining the temperature at 0° C. Upon complete addition, the reaction mixture was warmed to 20° C. and stirred overnight.

The reaction mixture was concentrated in vacuo and purged with toluene (3×0.6 v/w) to ensure removal of residual TFA. The product was obtained as a cream solid.

Step 3: Ethyl 1-acetyl-4-oxocyclohexanecarboxylate

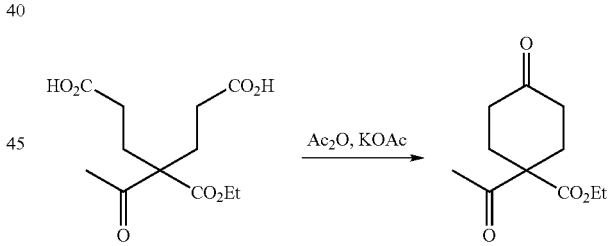

To a stirred suspension of Step 2 product (1 eq) in acetic anhydride (2.5 v/w) under nitrogen was added potassium acetate (0.02 eq). The reaction mixture was heated to, and stirred at the reflux temperature (145° C.) for 2 hours. The resultant solution was concentrated in vacuo, and purged with toluene to afford a brown oil.

This brown oil was dripped into an evacuated flask (at approximately 10 mmHg pressure) containing sand heated to 250° C.; the rate of addition was such that it equalled the rate of pyrolysate collection. Upon complete addition the vacuum was hardened to approximately 3 mmHg pressure, and the pyrolysis continued for a further 30 mins.

The pyrolysate was re-distilled at 106-110° C. at 0.5 mmHg to give the product as a colourless oil.

Step 4: Ethyl 4-methoxy-2-oxo-bicyclo[2.2.2]octane-1-carboxylate

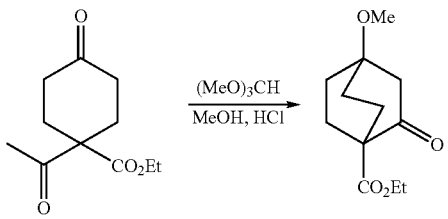

To a stirred solution of Step 3 product (1 eq) and trimethyl orthoformate (4.00 eq) in MeOH (9.4 v/w) at 5° C. was bubbled HCl gas (approximately 5 eq) over 2 hours, maintaining a pot temperature of 5° C. Upon complete addition, the reaction mixture, under nitrogen, was heated to, and stirred at, reflux for 30 minutes.

The resultant purple solution was cooled to approximately 30° C. and concentrated in vacuo. The residue was partitioned between saturated aqueous $NaHCO_3$ (20 v/w) and MTBE (8 v/w), and the separated aqueous layer extracted further with MTBE (3×8 v/w). The combined organic phases were washed with brine (12 v/w), dried over $MgSO_4$, filtered and concentrated in vacuo to afford the product as an amber oil which partially crystallised on standing.

Step 5: Ethyl 4-methoxy-2-trifluoromethanesulfonyloxybicyclo[2.2.2]oct-2-ene-1-carboxylate

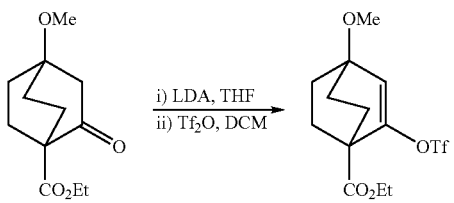

To a stirred solution of dry diisopropylamine (1.11 eq) in dry THF (16.3 v/w), under nitrogen, was added 2.5M butyl lithium (1.10 eq), and the resultant solution stirred for 30 minutes, maintaining the internal temperature at <−70° C. throughout.

A solution of Step 4 product (1 eq) in dry THF (6.3 v/w) was charged to the vessel at a reaction temperature of <−70° C. and the batch stirred at −70° C. to −75° C. for a further 30 minutes.

A solution of triflic anhydride (1.10 eq) in dry DCM (2.0 v/w) was added to the reaction mixture and it was stirred under nitrogen for 1 hour, maintaining the pot temperature at <−70° C. and then warmed to 20° C. and stirred for a further 60 minutes.

EtOAc (37 v/w) was added and the diluted solution was washed with 1M HCl (2×7.1 v/w), 1M NaOH (2×7.1 v/w) and brine (3.6 v/w). The separated organic phase was dried over $MgSO_4$, filtered and concentrated in vacuo to afford the crude product. The latter was purified by pad chromatography (5 w/w silica on crude), eluting with 2%→5% EtOAc in hexane.

Pure product-containing fractions were combined and concentrated in vacuo to afford the desired product as a colourless oil.

Step 6: Ethyl 4-methoxy-2-oxobicyclo[2.2.2]octane-1-carboxylate

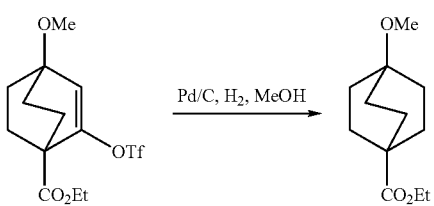

To a pressure hydrogenation vessel purged with nitrogen was charged methanol (10 v/w), 10% Pd/C catalyst (0.3 w/w) suspended in methanol (4 v/w) and Step 5 product (1 eq) dissolved in methanol (4 v/w). The reactor was sealed and purged with nitrogen (×5), purged with hydrogen (×3), and pressurised to 2 bar with hydrogen. The reaction mixture was stirred vigorously at 25-30° C. for two hours.

The reactor was vented and purged with nitrogen. The contents were removed and filtered through Celite. The cake was washed with methanol (10 v/w), and the combined filtrates and washings concentrated in vacuo.

The residue was dissolved in DCM (12 v/w) and washed with saturated aqueous $NaHCO_3$ (12 v/w+4 v/w). The combined aqueous phases were back-extracted with DCM (4 v/w) and the combined organic phases dried over $MgSO_4$, filtered and concentrated in vacuo to afford the crude product. This was purified by flash chromatography (8 w/w silica on crude), eluting with 5%→10% EtOAc in hexane. Product-containing fractions were combined and concentrated in vacuo to afford a mixture of methyl and ethyl esters (NMR) as a yellow oil.

Step 7

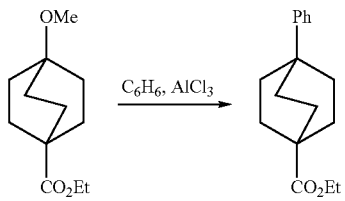

To a stirred suspension of $AlCl_3$ (3.74 eq) in benzene (4 v/w) at 7° C., under nitrogen, was added a solution of Step 6 product (1 eq) in benzene (1.8 v/w), maintaining an internal temperature of 7° C. Upon completion of addition, the reaction mixture was stirred at 7° C. for 40 minutes, then warmed to 20° C. and stirred at ambient temperature overnight. The batch was heated to, and stirred at, 60° C. for 4 hours, cooled to room temperature and poured onto ice (12 w/w). The two-phase mixture was extracted with EtOAc (1×12 v/w and 2×20 v/w), and the combined organic phases dried over $MgSO_4$, filtered and concentrated in vacuo to give a brown paste characterised as a mixture of the product esters (same proportion as of the input material).

The invention claimed is:
1. A compound of formula (I)

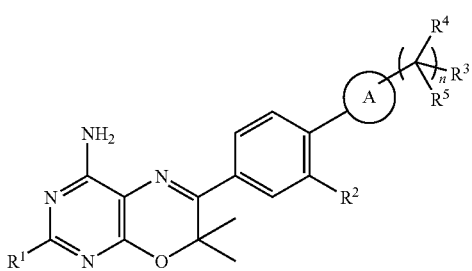

or a salt thereof,
wherein:
R$^1$ is selected from hydrogen, methyl and trifluoromethyl;
R$^2$ is hydrogen, chloro or fluoro;
Ring A is 1,4-bicyclo[2.2.2]octanediyl; 1,5-bicyclo[3.2.1]octanediyl; 1,5-bicyclo[3.2.2]nonanediyl or adamantyl;
R$^3$ is carboxy;
R$^4$ and R$^5$ are each independently hydrogen or methyl; and
n is 0 or 1.

2. The compound as claimed in claim 1 or a salt thereof wherein R$^1$ and R$^2$ are both hydrogen.

3. The compound as claimed in claim 1 or a salt thereof which is any one or more of:
{4-[4-(4-Amino-7,7-dimethyl-7H-pyrimido[4,5-b][1,4]oxazin-6-yl)phenyl]bicyclo[2.2.2]oct-1-yl}acetic acid; and/or
{3-[4-(4-amino-7,7-dimethyl-7H-pyrimido[4,5-b][1,4]oxazin-6-yl)phenyl]-1-adamantyl}acetic acid;
3-[4-(4-amino-7,7-dimethyl-7H-pyrimido[4,5-b][1,4]oxazin-6-yl)phenyl]adamantane-1-carboxylic acid;
2-{4-[4-(4-amino-7,7-dimethyl-7H-pyrimido[4,5-b][1,4]oxazin-6-yl)phenyl]bicyclo[2.2.2]oct-1-yl}propanoic acid;
{5-[4-(4-amino-7,7-dimethyl-7H-pyrimido[4,5-b][1,4]oxazin-6-yl)phenyl]bicyclo[3.2.2]non-1-yl}acetic acid; and
4-[4-(4-amino-7,7-dimethyl-7H-pyrimido[4,5-b][1,4]oxazin-6-yl)phenyl]bicyclo[2.2.2]octane-1-carboxylic acid.

4. A pharmaceutical composition comprising a compound of formula (I) as claimed in any one of claims 1, 2 and 3 or a pharmaceutically-acceptable salt thereof, in association with a pharmaceutically-acceptable excipient or carrier.

* * * * *